United States Patent
Liang et al.

(10) Patent No.: US 10,829,466 B2
(45) Date of Patent: Nov. 10, 2020

(54) STILBENE DERIVATIVE AND PREPARATION METHOD THEREOF

(71) Applicant: BEIJING INSTITUTE OF TECHNOLOGY, Beijing (CN)

(72) Inventors: Jianhua Liang, Beijing (CN); Hong Qing, Beijing (CN); Si Wu, Beijing (CN); Sisi Liu, Beijing (CN); Nuomin Li, Beijing (CN); Liang Yang, Beijing (CN)

(73) Assignee: BEIJING INSTITUTE OF TECHNOLOGY, Beijing (CN)

(*) Notice: Subject to any disclaimer, the term of this patent is extended or adjusted under 35 U.S.C. 154(b) by 189 days.

(21) Appl. No.: 16/067,816

(22) PCT Filed: Oct. 26, 2016

(86) PCT No.: PCT/CN2016/103442
§ 371 (c)(1),
(2) Date: Jul. 2, 2018

(87) PCT Pub. No.: WO2017/113964
PCT Pub. Date: Jul. 6, 2017

(65) Prior Publication Data
US 2020/0148662 A1   May 14, 2020

(30) Foreign Application Priority Data

Dec. 31, 2015  (CN) .......................... 2015 1 1032690

(51) Int. Cl.
*C07D 317/50* (2006.01)
*C07D 405/12* (2006.01)
(Continued)

(52) U.S. Cl.
CPC ......... *C07D 317/50* (2013.01); *C07D 405/12* (2013.01); *C07D 407/12* (2013.01); *C07D 409/12* (2013.01)

(58) Field of Classification Search
CPC ... C07D 409/12; C07D 407/12; C07D 405/12
(Continued)

(56) References Cited

FOREIGN PATENT DOCUMENTS

| CN | 101432011 A | 5/2009 |
| CN | 106008487 A | 10/2016 |

(Continued)

OTHER PUBLICATIONS

Karen S. MacMillan et al, Development of Proneurogenic, Neuroprotective Small Molecules, J. Am. Chem. Soc., 133 (2011) 1428-1437.
(Continued)

*Primary Examiner* — Taylor V Oh
(74) *Attorney, Agent, or Firm* — Bayramoglu Law Offices LLC

(57) ABSTRACT

A stilbene derivative, which is a compound of the following general formula I or general formula II, or an acceptable salt formed by the compound of the general formula I or the general formula II and an inorganic or organic acid;

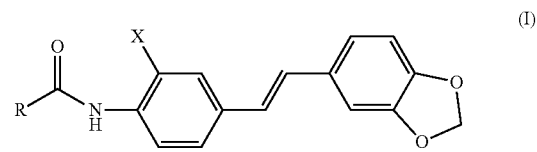

(Continued)

```
┌─────────────────────────────────────────┐    101
│    Preparation of crude compound        │───/
└─────────────────────────────────────────┘
                     │
┌─────────────────────────────────────────┐    102
│    Preparation of compound              │───/
└─────────────────────────────────────────┘
```

-continued

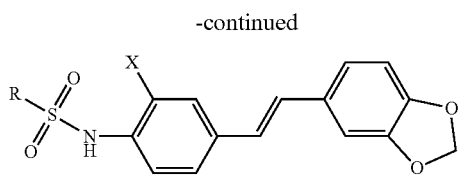

(II)

wherein, in the general formula I or the general formula II, the atom represented by X is a hydrogen atom or a halogen atom;
the substituent represented by R is C1-C6 alkyl, 1-6-membered heteroalkyl, C2-C4 alkenyl, C2-C4 alkynyl, C3-C6 cycloalkyl, substituted C3-C6 cycloalkyl, 3-6-membered heterocycloalkyl, substituted 3-6-membered heterocycloalkyl, 5-18-membered aryl, substituted 5-18-membered aryl, 5-18-membered heteroaryl, or substituted 5-18-membered heteroaryl.

20 Claims, 3 Drawing Sheets

(51) Int. Cl.
*C07D 407/12* (2006.01)
*C07D 409/12* (2006.01)

(58) Field of Classification Search
USPC .......................................................... 546/197
See application file for complete search history.

(56) References Cited

FOREIGN PATENT DOCUMENTS

| WO | 03009807 A2 | 2/2003 |
| WO | 2007100775 A2 | 9/2007 |
| WO | 2015014768 A1 | 2/2015 |

OTHER PUBLICATIONS

Chunmei Zhao et al, Mechanisms and Functional Implications of Adult Neurogenesis, Cell, 132 (2008) 645-660.

STILBENE DERIVATIVE AND PREPARATION METHOD THEREOF

CROSS REFERENCE TO THE RELATED APPLICATIONS

This application is the national phase entry of the International Application no. PCT/CN2016/103442, filed on Oct. 26, 2016, which claims the priority of Chinese Patent Application No. 201511032690.X entitled "Novel stilbene derivative and Preparation Method Thereof", filed with the Chinese Patent Office on Dec. 31, 2015, the content of which is incorporated herein with reference to its entirety.

TECHNICAL FIELD

The present invention relates to the field of chemical synthesis and pharmaceuticals, in particular to a novel stilbene derivative and a preparation method of the novel stilbene derivative.

BACKGROUND

Alzheimer's disease (AD) is a neurodegenerative disease of the central nervous system. It is manifested as an occult cognitive decline in the early stages and then develops into severe memory loss, behavioral and personality changes, speech disorders and loss of independent living ability within 5-10 years. In 2015, 46.8 million cases were registered globally and were listed as the fourth most common cause of death after cardiovascular diseases, stroke and tumors. There are no clinical cures. The incidence of Alzheimer's disease is closely related to age. With the increase of age, the incidence of AD increases exponentially. According to statistics, the incidence of AD is about 1% for people about 60 years old, and the incidence will double every 5-6 years on average after that. As the ageing of the population intensifies, the incidence of Alzheimer's disease is going to get higher and higher and the progressive memory, learning ability, and daily living ability will decline, which will seriously affect the quality of life of the elderly and bring a heavy burden for their families and society.

The basic pathological changes in the brains of AD patients are amyloid plaques, neurofibrillary tangles and neuron loss. A large number of animal experiments have demonstrated that in normal adult mammals, neural progenitor cells have a unique ability to proliferate and differentiate into mature neurons when the sub-ventricular zone (SVZ) and the sub-granular zone (SGZ) of the dentate gyrus are stimulated by certain external conditions. Hippocannpal neurogenesis can be examined at the present stage mainly by a BrdU (5-bromodeoxyuridine) labeling method. BrdU is a thymidine analog that can be integrated into the double-stranded DNA of cleavage cells in the S phase, and the in vivo changes of labeled cells can be detected by immuno-histochemical fluorescent staining. BrdU positive cells can be regarded as cells having proliferative activity and are the most commonly used markers in neural stem cell research. The loss of body functions caused by impaired brain neuron function or neuronal death caused by individual aging or lesions is manifested as decreased learning and memory ability, spatial cognitive impairment and impaired physical exercise function. As the hippocampal function is closely related to learning and memory, and cognitive ability, it is expected that new neurons can be established by neurogenesis to replace impaired or apoptotic neurons, allowing Alzheimer's patients to restore their physiological function and regain their high-quality life.

Through randomly screening known drugs, people discover some compounds that have neurogenesis, such as curcumin, nodakenin, resveratrol and aminopropyl carbazole. Some Chinese herbal extracts, such as ginkgo leaf extracts have also been discovered. Animal behavior experiments show that neurogenesis can indeed improve memory, learning and cognitive abilities of animals.

The improvement of adult hippocampal endogenous neurogenesis through small molecule stimulation has great potential for the treatment of Alzheimer's disease and neurodegenerative diseases (see J. Am. Chem. Soc., 133 (2011) 1428-1437; Cell, 132 (2008) 645-660; WO2015014768-A1).

However, there are still several important issues that need to be resolved urgently in the current research on neurogenesis: 1) the vast majority of studies are random trial-and-error screening and seldom involve reports with common groups (especially pharmacophores), which are not conducive to the further design and screening of compounds with higher activity; 2) most of the studies are based on the screening of other known targets or other compounds with pharmacological activity, so these pharmacological side effects will limit the clinical application in the treatment of dementia; 3) Blood-Brain Barrier is an important barrier to nervous drugs; many drugs do not meet the optimal physico-chemical properties breaking through the blood-brain barrier structurally. For example, they contain too many hydrogen bond donors-hydroxyl or amino groups, resulting in low permeability and ineffective passage of lipophilic blood-brain barrier, and they are eventually manifested at very large doses (for example, the intraperitoneal injection dose of resveratrol with three phenolic hydroxyl groups is 40 mg/Kg), which inevitably limits future clinical applications and requires structural modifications.

To sum up, one technical problem that needs to be urgently resolved by those skilled in the art is how to provide a type of novel compounds, which have a common pharmacophore, and such molecules have a low toxicity to nerve cells and can pass the blood-brain barrier effectively and thus can promote neurogenesis in the sub-granular zone of dentate gyrus at lower doses.

SUMMARY

The technical problem to be resolved by the present invention is to provide a compound having neurogenesis activity and a preparation method of a novel stilbene derivative compound having neurogenesis activity, and also provide a novel stilbene derivative having neurogenesis activity, and a preparation method of a novel stilbene derivative having neurogenesis activity.

In order to resolve the above problem, the present invention discloses a novel stilbene derivative, which is a compound of the following general formula I or general formula II, or the novel stilbene derivative is an acceptable salt formed by the compound of the general formula I or the general formula II and an inorganic or organic acid;

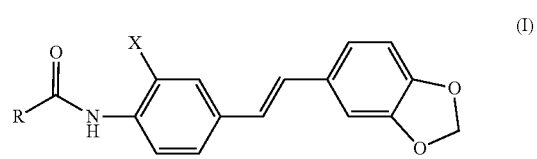

(I)

-continued

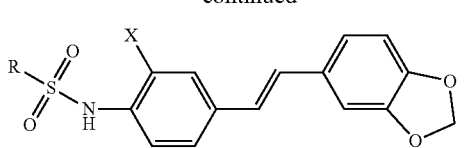

In the general formula I or the general formula II, the atom represented by X is a hydrogen atom or a halogen atom;

the substituent represented by R is C1-C6 alkyl, 1-6-membered heteroalkyl, C2-C4 alkenyl, C2-C4 alkynyl, C3-C6 cycloalkyl, substituted C3-C6 cycloalkyl, 3-6-membered heterocycloalkyl, substituted 3-6-membered heterocycloalkyl, 5-18-membered aryl, substituted 5-18-membered aryl, 5-18-membered heteroaryl, or substituted 5-18-membered heteroaryl;

the novel stilbene derivatives have neurogenesis activity and low neuronal cytotoxicity.

The present invention further discloses a novel stilbene derivative, which is a compound of the following general formula I or general formula II, or an acceptable salt formed by the compound of the general formula I or the general formula II and an inorganic or organic acid;

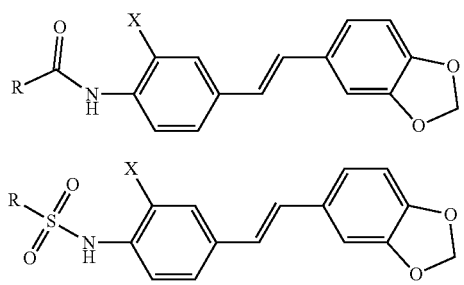

In the general formula I or the general formula II, the atom represented by X is a hydrogen atom or a halogen atom;

the substituent represented by R is a substituted C2-C4 alkenyl.

The invention further discloses a preparation method of the above novel stilbene derivative, wherein the preparation method of the compound of the general formula I or the general formula II comprises:

preparation of a crude compound: dissolving a reaction substrate in dichloromethane and adding a catalyst to obtain a mixture, and adding an acylating agent or a treated acylating agent drop by drop to the mixture and stirring until the end of the reaction, and evaporating the dichloromethane off to obtain the crude compound, wherein the reaction substrate is E-4'-amino-3,4-methylenedioxystilbene or E-3,4-methylenedioxy-3'-fluoro-4'-amino-stilbene; and preparation of a compound: adding a saturated NaHCO₃ solution to the crude compound, adding dichloromethane for extraction to obtain an organic phase at the bottom, washing the organic phase with distilled water and saturated brine in turn, and concentrating by rotary evaporation and drying the washed organic phase to obtain a solid substance, and then carrying out column chromatography on the resulting solid substance to obtain a compound having neurogenesis activity and low neuronal cytotoxicity.

Herein, when the acylating agent is an anhydride or acyl chloride, the preparation method of the crude compound comprises:

dissolving the reaction substrate in dichloromethane, adding pyridine and 4-dimethylaminopyridine to obtain a mixture, and cooling the mixture in a cold water bath to below 0° C., adding the acylating agent drop by drop to the mixture that is always lower than 0° C. and stirring until the end of the reaction, and evaporating the dichloromethane off to obtain the crude compound;

when the acylating agent is an acid, the method for preparing the crude compound comprises:

dissolving the acylating reagent in dichloromethane, adding triethylamine, stirring and dissolving, then adding pivaloyl chloride and stirring to dissolve the pivaloyl chloride to obtain the treated acylating reagent;

dissolving the reaction substrate in dichloromethane, and adding the treated acylating agent drop by drop, resting at room temperature until the end of the reaction, and evaporating the dichloromethane off to obtain the crude compound;

the method further comprises:

preparation of an acceptable salt: adding an inorganic or organic acid to the resulting compound to obtain an acceptable novel stilbene derivative with neurogenesis activity and low neuronal cytotoxicity.

The present invention further discloses the application of the above-mentioned compound of the general formula I or the general formula II or a pharmaceutically acceptable salt thereof as an active ingredient in the preparation of anti-Alzheimer's drugs and anti-neurodegenerative drugs.

The present invention further discloses the application of the above-mentioned compound of the general formula I or the general formula II or a pharmaceutically acceptable salt thereof as anti-Alzheimer's drugs and anti-neurodegenerative drugs.

The present invention further discloses a method for treating Alzheimer's disease and treating neurodegenerative diseases. The method comprises administering to a patient a therapeutically effective dose of the compound of the general formula I or the general formula II, or a pharmaceutically acceptable salt thereof.

Compared with the prior art, the present invention has the following advantages:

Through multiple experiments and theoretical studies, it is found in the present invention that the compound of the general formula (I) or the general formula (II) has a novel structure, and the novel stilbene derivative has better neurogenesis activity on the basis of the novel structure.

In addition, in terms of biological toxicity, the novel stilbene derivative in the present invention has low toxicity to nerve cells and less damage to nerve cells, and has important biological significance. For example, E-4'-amino-3,4-methylenedioxy-stilbene (WS-4) has high neuronal cytotoxicity through in vitro tests, and under the test conditions in embodiments of the present invention, the cell survival rates are all less than 50% at a high dose, a medium dose and a low dose, and the neuronal cytotoxicity of the compound after acylation is reduced to some degree, and especially for E-4'-acetylamino-3,4-methylenedioxy-stilbene (WS-6), E-4'-benzoylamino-3,4-methylenedioxy-stilbene (WS-70), and E-4'-cyclopropylcarboxamino-3,4-methylenedioxy-stilbene (WS-74), the neuronal cytotoxicity is greatly reduced and the cell survival rates exceeded 80% at all doses.

In addition, when compared with the resveratrol already reported, the novel stilbene derivative of the present invention can exhibit significant neurogenesis activity at a lower dose, for example, the novel stilbene derivative is administrated through intraperitoneal injections for 28 days, at a dose of 2 mg/Kg or 4 mg/Kg. Resveratrol exhibits neurogenesis activity only in the case of a high dose of 40 mg/Kg. Therefore, the dose of the novel stilbene derivative of the present invention is relatively low.

Experimental studies have shown that, even at the same dose, changing the groups of the stilbene compound causes a significant change in the neurogenesis activity of the compound because there is no known rule to follow between the neurogenesis activity of a selected group and the compound. As a result, the novel stilbene derivative having neurogenesis activity in the present invention cannot be directly derived from the prior art. In addition, the present invention has broken through the knowledge of the structure-activity relationship of existing stilbene structures. Studies have shown that stilbene structures containing specific substituents have low neuronal cytotoxicity, high neurogenesis activity and the structural advantage in the ability to cross the blood-brain barrier. However, the structural advantage is not disclosed in the reports with respect to the structure and properties of stilbene in the prior art. Therefore, the stilbene derivative having the general formula I or the general formula II of the present invention is novel and involves an inventive step.

DETAILED DESCRIPTION

Figure 1:
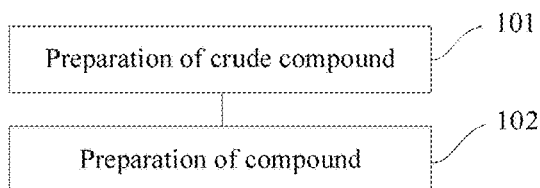
FIG. 1 is a flow chart of a preparation method of a novel stilbene derivative according to Embodiment 1 of the present invention.

To make the foregoing objectives, features and advantages of the present invention clearer and more understandable, the present invention will be further described with reference to the accompanying drawings and specific embodiments.

The present invention provides a novel stilbene derivative, which is a compound of the following general formula I or general formula II, or an acceptable salt formed by the compound of the general formula I or the general formula II and an inorganic or organic acid; the salt acts as a prodrug to release the free base shown by the general structure under in vivo physiological conditions and acts as an active ingredient to take a pharmacological effect.

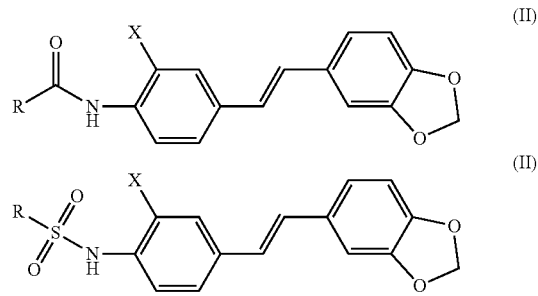

In the general formula I or the general formula II, the atom represented by X is a hydrogen atom or a halogen atom;

the substituent represented by R is C1-C6 alkyl, 1-6-membered heteroalkyl, C2-C4 alkenyl, C2-C4 alkynyl, C3-C6 cycloalkyl, substituted C3-C6 cycloalkyl, 3-6-membered heterocycloalkyl, substituted 3-6-membered heterocycloalkyl, 5-18-membered aryl, substituted 5-18-membered aryl, 5-18-membered heteroaryl, or substituted 5-18-membered heteroaryl;

the novel stilbene derivatives have neurogenesis activity and low neuronal cytotoxicity.

The term "aryl" as used in the embodiments of the present invention refers to an aromatic carbocyclic group having one monocyclic ring or two or more fused rings. The aryl preferably has 5-18, 5-14, 5-10, 5-8, 5-6, or 6 carbon atoms. Typical examples of the "aryl" include, but are not limited to, phenyl, naphthyl, anthryl and the like. The "aryl" is most preferably phenyl or naphthyl.

The term "heteroaryl" as used in the embodiments of the present invention denotes the aryl as defined in the embodiments of the present invention in which one or two or more carbon atoms are substituted by one or two or more heteroatoms independently selected from O, S, or N. The heteroaryl is preferably 5-18, 5-14, 5-10, 5-8, 5-6 or 5 or 6-membered heteroaryl. Typical examples of the "heteroaryl" include but are not limited to furyl, pyrrolyl, thienyl, imidazolyl, triazolyl, tetrazolyl, pyrazolyl, oxazolyl, isoxazolyl, thiazolyl, pyridyl, pyrazinyl, pyrimidinyl, pyridazinyl, triazinyl, benzofuranyl, isobenzofuranyl, indenyl, isodecyl, benzo[b]thienyl, benzo[c]thienyl, benzimidazolyl, purinyl, indazolyl, benzoxazolyl, benzoisoxazolyl, benzothiazolyl, quinolinyl, isoquinolinyl, quinazolinyl, benzopyrazinyl, benzopyridazinyl, pyridopyridyl and the like. The "heteroaryl" is preferably furyl, pyrrolyl, thienyl, pyridyl, quinolinyl or isoquinolinyl. The preferred "heteroaryl" is a 5-6-membered heteroaryl, and preferably the 5-6-membered heteroaryl is thienyl or pyridinyl.

The above-mentioned various heteroaryls are only used as examples, and other non-enumerated heteroaryls also have similar properties and the details thereof are not described herein for the sake of brevity.

The term "Ca-Cb alkyl" (a and b are numbers) as used in the embodiments of the present invention refers to a saturated linear or branched alkyl having a-b carbon atoms, such as C1-C6 alkyl and C1-C4 alkyl. The preferred C1-C6 alkyl is methyl, ethyl, n-propyl, isopropyl, sec-butyl, tert-butyl, tert-amyl or neopentyl. The preferred C1-C4 alkyl is methyl, ethyl, n-propyl, isopropyl or tert-butyl, more preferably methyl, ethyl, n-propyl or isopropyl. The above-mentioned various alkyls are used only as examples, and other non-enumerated alkyls also have similar properties, and the details thereof are not described herein for the sake of brevity.

The term "a-b-membered heteroalkyl" (a and b are numbers) used in the embodiments of the present invention refers to Ca-Cb alkyl containing one or more heteroatoms independently selected from N, O and S, as defined in the embodiments of the present invention, such as 1-6-membered heteroalkyl, and 3-5-membered heteroalkyl. The preferred number of N, O and S heteroatoms is 1-2. The preferred heteroalkyl is N,N-dimethylamino, N-methyl-N-ethyl amino, N,N-dimethylaminomethyl, N,N-diethylamino, methoxy, ethoxy, isopropoxy or tert-butoxy. The further preferred heteroalkyl is 3-5-membered heteroalkyl, and the 3-5-membered heteroalkyl is preferably N, N-dimethylamino. The above-mentioned various heteroalkyls are only used as examples, and other non-enumerated heteroalkyls also have similar properties and the details thereof are not described herein for the sake of brevity.

The term "C2-C4 alkenyl" used in the embodiments of the present invention refers to an olefinically unsaturated linear or branched alkyl containing at least one carbon-carbon double bond (—C═C—), and having 2-4 carbon atoms. The preferred alkenyl is vinyl or propenyl. The term "C2-C4 alkynyl" used in the embodiments of the present invention refers to an acetylenically unsaturated linear or branched alkyl containing at least one carbon-carbon triple bond (—C≡C—) and having 2-4 carbon atoms. The preferred alkynyl is ethynyl or propynyl. The above-mentioned various alkenyls and alkynyls are only used as examples, and other non-enumerated alkenyls and alkynyls also have similar properties, and the details thereof are not described herein for the sake of brevity.

The term "C3-C6 cycloalkyl" used in the embodiments of the present invention refers to a saturated cyclic alkyl having 3-6 carbon atoms. The preferred cycloalkyl is cyclopropyl, cyclobutyl, cyclopentyl or cyclohexyl, and further preferably is cyclopropyl or cyclobutyl. The term "3-6-membered heterocycloalkyl" used in the embodiments of the present invention refers to a C3-C6 cycloalkyl containing one or more heteroatoms independently selected from N, O and S, as defined in the embodiments of the present invention. The preferred heterocycloalkyl is tetrahydrofuranyl, pyrrolidinyl, piperidinyl, morpholinyl or piperazinyl. Further, the heterocycloalkyl is preferably 5-6-membered heterocycloalkyl; the 5-6-membered heterocycloalkyl is preferably tetrahydrofuranyl or pyrrolidinyl, where the substituted position of the pyrrolidinyl may be on the 1-position N. The above-mentioned various cycloalkyls are only used as examples, and other non-enumerated cycloalkyls also have similar properties, and the details thereof will not be repeated herein for the sake of brevity.

The term "halogen" used in the embodiments of the present invention refers to fluorine, chlorine, bromine or iodine. The preferred halogen is fluorine and chlorine.

As for the terms "substituted" cycloalkyl, "substituted" heterocycloalkyl, "substituted" aryl, "substituted" heteroaryl, etc. used in the embodiments of the present invention, "substituted" means that a compound or group is substituted by one or two or more substituents independently selected from the following substituents: aryl (e.g., phenyl), heteroaryl (e.g., furyl, pyrrolyl, thienyl, pyridyl, quinolinyl, isoquinolinyl), C3-C6 cycloalkyl, 3-6-membered heterocycloalkyl, C1-C6 alkyl, C2-C4 alkenyl, C2-C4 alkynyl, 1-6-membered heteroalkyl, nitro, cyano, hydroxy, halogen, amino and so on. The preferred number of substituents is 1-2.

The preferred "substituted C3-C6 cycloalkyl" is methylcyclopropyl, fluorocyclopropyl, cyanocyclopropyl, cyclopropylmethyl or (cyclohexyl)ethyl. Further preferably, the substituted C3-C6 cycloalkyl is a substituted C3 cycloalkyl, and the substituted C3 cycloalkyl is preferably cyanocyclopropyl.

The preferred "substituted 3-6-membered heterocycloalkyl" is N-methylpiperidinyl, N-ethylpiperidinyl, N-acetylpiperidinyl, or (N-methylpiperidinyl) piperidinyl.

Preferably, the substituted aryl is a substituted 6-10-membered aryl, further preferably a substituted 6-membered aryl. The substituted 6-membered aryl is substituted phenyl, and the preferred "substituted phenyl" is preferably methylphenyl, dimethylphenyl, fluorophenyl, chlorophenyl, bromophenyl, isopropylphenyl, tertiary aminophenyl, methoxyphenyl, dimethoxyphenyl, acetylphenyl, cyanophenyl, (R)-1-phenyl-1-methoxymethyl, (S)-1-phenyl-1-methoxymethyl, benzyl, methoxybenzyl, methylbenzyl, tertiary aminobenzyl, fluorobenzyl, chlorobenzyl, or cyanobenzyl. Further preferably, the substituted phenyl is benzyl, methylphenyl, fluorophenyl, chlorophenyl or cyanophenyl.

The preferred "substituted naphthyl" is methoxynaphthyl, methylnaphthyl, tertiary aminonaphthyl, fluoronaphthyl, chloronaphthyl, or cyanonaphthyl.

The preferred "substituted thienyl" is methoxythienyl, methylthienyl, fluorothienyl, chlorothienyl or cyanothienyl.

The preferred "substituted furyl" is methoxyfuryl, methylfuryl, fluorofuryl, chlorofuryl or cyanofuryl.

The preferred "substituted pyridyl" is methylpyridyl, methoxypyridyl, fluoropyridyl, chloropyridyl, cyanopyridyl, pyridylmethyl, (pyridyl)ethyl or (pyridylsulfydryl)methyl.

The preferred "substituted quinolinyl" is methoxyquinolinyl, methylquinolinyl, fluoroquinolinyl, chloroquinolinyl, or cyanoquinolinyl.

The preferred "substituted isoquinolinyl" is methoxyisoquinolinyl, methylisoquinolinyl, fluoroisoquinolinyl, chloroisoquinolinyl or cyanoisoquinolinyl.

Further preferably, the substituted heteroaryl is a substituted 5-10-membered heteroaryl, further preferably a substituted 6-membered heteroaryl, and the substituted 6-membered heteroaryl is preferably a pyridylmethyl.

The preferred "substituted C2-C4 alkenyl" is 2,2-dialkylvinyl, 6-membered arylvinyl, substituted 6-membered arylvinyl, or 5-6-membered heteroarylvinyl. Further preferably, the substituted C2-C4 alkenyl is 2,2-dimethylvinyl, phenylvinyl, p-tolylvinyl, p-chlorophenylvinyl, p-fluorophenylvinyl, p-cyanophenylvinyl or pyridylvinyl.

The above-mentioned various substituted compounds are merely used as examples. In the same classification, other non-enumerated substituted compounds have similar properties and the details thereof are not described herein for the sake of brevity.

Through multiple experiments and theoretical studies, it is found in the present invention that the compound of the general formula (I) or the general formula (II) has a novel structure, and the novel stilbene derivative has better neurogenesis activity on the basis of the novel structure.

The structural research shows that at the same dose, changing the group of the general formula (I) or the general formula (II) in the embodiments of the present invention may cause the neurogenesis activity of the compound to significantly change. Taking E-4'-acetamino-3,4-methylenedioxystilbene (WS-6) as an example, WS-6 has a better neurogenesis activity. Under the test conditions of the embodiments of the present invention, the 4'-acetylamino group is changed to a hydroxyl or an acetoxy or a tertiary amino, and the other structures are not changed, and then corresponding compounds E-4'-hydroxy-3,4-methylenedioxy-stilbene (WS-11), E-4'-acetoxy-3,4-methylenedioxy-stilbene (WS-10), and E-4'-tertamino-3,4-methylenedioxy-stilbene (WS-60) are obtained, respectively, in which WS-10 and WS-11 have no neurogenesis activity, and WS-60 has a weak neurogenesis activity. The 3,4-methylenedioxy structure is cut to form a 3,4-dimethoxy and the other structures are not changed. The resulting E-4'-acetylamino-3,4-dimethoxy-stilbene (WS-43) also has no significant neurogenesis activity. The intermediate linking group, i.e., ethylene, is changed into ethyl or ethynyl to obtain E-4'-acetamino-3,4-methylenedioxy-diphenylethane (WS-35), and E-4'-acetamino-3,4-methylenedioxy-diphenylacetylene (WS-77), respectively, in which WS-35 has no neurogenesis activity, and WS-77 has a weak neurogenesis activity. E-4'-(N-acetyl-N-methylamino)-3,4-methylenedioxy-stilbene (WS-80) which is obtained by substituting hydrogen on the 4'-acetylamino N of WS-6 by a methyl has no significant neurogenesis activity.

Therefore, the novel stilbene derivatives having better neurogenesis activity in the embodiments of the present invention are created through a great deal of labor.

In addition, in terms of biological toxicity, the novel stilbene derivative in the present invention has low toxicity to nerve cells and less damage to nerve cells, and has important biological significance. For example, E-4'-amino-3,4-methylenedioxy-stilbene (WS-4) has high neuronal cytotoxicity through in vitro tests, and under the test conditions in embodiments of the present invention, the cell survival rates are all less than 50% at a high dose, a medium dose and a low dose, and the neuronal cytotoxicity of the compound after acylation is reduced and the cell survival rates of some of the compounds are all over 80% at all doses.

Experimental studies have shown that there is no correspondence between low neuronal cytotoxicity and a substance structure, although the novel stilbene derivative having the general formula (I) or (II) in the present invention has low neuronal cytotoxicity, substances similar in structure to the compounds of the present invention do not have low neuronal cytotoxicity. For example, if the acetylamino in the molecule E-4-acetylamino-3',4'-methylenedioxy-stilbene (WS-6) is shifted from 4- to 3-position and the others are unchanged, the resulting molecule E-3-acetylamino-3',4'-methylenedioxy-stilbene (WS-49) has higher neuronal cytotoxicity and the cell survival rates do not exceed 20% at all doses. Another example is the insertion of a carbonyl on the olefin between two benzene rings of stilbene and the resulting 4-acetylamino-3',4'-methylenedioxychalcone (WS-37) also has a higher neuronal cytotoxicity, and its cell survival rates are all less than 10% at all doses. Therefore, the novel stilbene derivative having low neuronal cytotoxicity according to the embodiments of the present invention is created through a great deal of labor.

In the embodiments of the present invention, preferably, the atom represented by X is a hydrogen atom or a fluorine atom;

the substituent represented by R is C1-C4 alkyl, 3-5-membered heteroalkyl, C3-C6 cycloalkyl, substituted C3-C6 cycloalkyl, 3-6-membered heterocycloalkyl, and substituted 3-6-membered heterocycloalkyl, 6-10-membered aryl, substituted 6-10-membered aryl, 5-10-membered heteroaryl, or substituted 5-10-membered heteroaryl.

In the embodiments of the present invention, preferably, the C1-C4 alkyl is methyl, ethyl, n-propyl, isopropyl or tert-butyl;

the 3-5-membered heteroalkyl is N,N-dimethylamino, N-methyl-N-ethylamino, N, N-dimethylaminomethyl, N, N-diethylamino, methoxy, ethoxy, isopropoxy or tert-butoxy;

the C3-C6 cycloalkyl is cyclopropyl, cyclobutyl, cyclopentyl or cyclohexyl;

the substituted C3-C6 cycloalkyl is methylcyclopropyl, fluorocyclopropyl, cyanocyclopropyl, cyclopropylmethyl or (cyclohexyl)ethyl;

the 3-6-membered heterocycloalkyl is tetrahydrofuranyl, pyrrolidinyl, morpholinyl, piperidinyl or piperazinyl.

the substituted 3-6-membered heterocycloalkyl is N-methylpiperidinyl, N-ethylpiperidinyl, N-acetylpiperidinyl, or (N-methylpiperidinyl) piperidinyl;

the 6-10 membered aryl is phenyl or naphthyl;

the substituted 6-10-membered aryl is substituted phenyl or substituted naphthyl;

the 5-10-membered heteroaryl is furyl, pyrrolyl, thienyl, pyridyl, quinolinyl or isoquinolinyl;

the substituted 5-10-membered heteroaryl is substituted furyl, substituted pyrrolyl, substituted thienyl, substituted pyridyl, substituted quinolinyl, or substituted isoquinolinyl.

In the embodiments of the present invention, preferably, the substituted phenyl is methylphenyl, dimethylphenyl, fluorophenyl, chlorophenyl, bromophenyl, isopropylphenyl, tertiary aminophenyl, methoxyphenyl, dimethoxyphenyl, acetylphenyl, cyanophenyl, (R)-1-phenyl-1-methoxymethyl or (S)-1-phenyl-1-methoxymethyl, benzyl, methoxybenzyl, methylbenzyl, tertiary aminobenzyl, fluorobenzyl, chlorobenzyl, or cyanobenzyl;

the substituted naphthyl is methoxynaphthyl, methylnaphthyl, tertiary aminonaphthyl, fluoronaphthyl, chloronaphthyl, or cyanonaphthyl;

the substituted furyl is methoxyfuryl, methylfuryl, fluorofuryl, chlorofuryl or cyanofuryl;

the substituted thienyl is methoxythienyl, methylthienyl, fluorothienyl, chlorothienyl or cyanothienyl;

the substituted pyridyl is methylpyridyl, methoxypyridyl, fluoropyridyl, chloropyridyl, cyanopyridyl, pyridylmethyl, (pyridyl)ethyl or (pyridyl sulfydryl)methyl;

the substituted quinolinyl is methoxyquinolinyl, methylquinolinyl, fluoroquinolinyl, chloroquinolinyl, or cyanoquinolinyl;

the substituted isoquinolinyl is methoxyisoquinolinyl, methylisoquinolinyl, fluoroisoquinolinyl, chloroisoquinolinyl or cyanoisoquinolinyl.

The preferred substituted C2-C4 alkenyl is 2,2-dimethylvinyl, phenylvinyl, p-tolylvinyl, p-chlorophenylvinyl, p-fluorophenylvinyl, p-cyanophenylvinyl or pyridylvinyl.

In the embodiments of the present invention, preferably, the compound of the general formula I or the general formula II is prepared by acylating E-4'-amino-3,4-methylenedioxy-stilbene or E-3,4-methylenedioxy-3'-fluoro-4'-amino-stilbene with an acylating agent.

In an embodiment of the present invention, preferably, the acylating agent is a carboxylic acid, an anhydride or an acyl chloride.

In the embodiments of the present invention, preferably, the carboxylic acid is 2-furancarboxylic acid, 2-thiophenecarboxylic acid, 2-picolinic acid, 2-tetrahydrofurancarboxylic acid, (R)-2-tetrahydrofurancarboxylic acid, (S)-2-tetrahydrofuran Formic acid, 1-methylpiperidine-4-carboxylic acid, cyclopropylacetic acid, 1-methylcyclopropanecarboxylic acid, 2-methylcyclopropanecarboxylic acid, 1-cyanocyclopropanecarboxylic acid, cyclopropylacetic acid, cyclobutanecarboxylic acid, cyclopentanecarboxylic acid, p-fluorophenyl acrylic acid, p-cyanophenylacrylic acid or pyridylacrylic acid;

the anhydride is benzoic anhydride, acetic anhydride, propionic anhydride, n-butyric anhydride, isobutyric anhydride, benzoic anhydride or di-tert-butyl dicarbonate;

the acyl chloride is a pivaloyl chloride, N,N-dimethylcarbamoyl chloride, benzenesulfonyl chloride, cyclopropylsulfonyl chloride, isopropylsulfonyl chloride, 4-methoxybenzoyl chloride, 4-cyanobenzoyl chloride, 4-chlorobenzenesulfonyl chloride, phenylacetyl chloride, benzylsulfonyl chloride, p-toluenesulfonyl chloride, 1-pyrrolidinecarbonyl chloride, N-acetylpiperidin-4-chloride, isopropyl chloroformate, dimethylaminosulfonyl chloride, 4-dimethylaminobenzoyl chloride, acryloyl chloride, 3,3-dimethylacryloyl chloride, cinnamoyl chloride, p-tolylacryloyl chloride, or p-chlorophenylacryloyl chloride.

Using conditions known in various documents, it is possible to convert s carboxylic acid to an acyl chloride or an anhydride to increase the reactivity or to increase the amide-forming ability by using various catalysts such as DCC, EDC or HOBt. Similarly, acyl chlorides and anhydrides can also be converted into suitable acylating reagents and then react with E-4'-amino-3,4-methylenedioxy-stilbene or E-3, 4-methylenedioxy-3'-fluoro-4'-amino-stilbene after being changed in the reactivity or selectivity of the reaction. Alternatively, a special precursor re-agent can be used for reaction in which, in addition to an amide-forming bond, other functional group transformations that occur simultaneously can change the precursor re-agent to a target acylation donor. For example, in a document, chloroacryloyl chloride may be substituted for acryloyl chloride under certain conditions to provide an acryloyl as a precursor re-agent.

In the embodiments of the present invention, preferably, the novel stilbene derivative of the general formula I or the general formula II or the compound forming the novel stilbene derivative is prepared by acylating the 4'-amino-3,4-methylenedioxy-stilbene with an acylating reagent;

when the carboxylic acid is 2-thiophenecarboxylic acid, 2-picolinic acid, cyclopropylacetic acid, cyclobutylcarboxylic acid, 2-tetrahydrofurancarboxylic acid, or 1-methylpiperidine-4-carboxylic acid, the structural formula of the compound is any of the following i-vi:

(i)

(ii)

(iii)

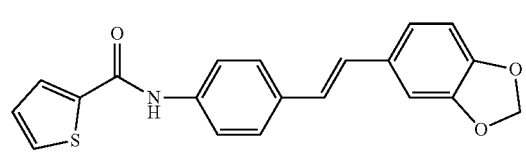

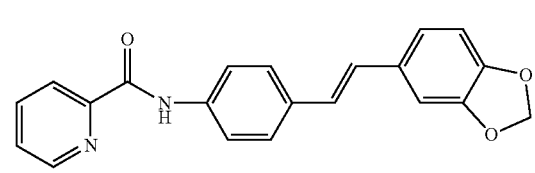

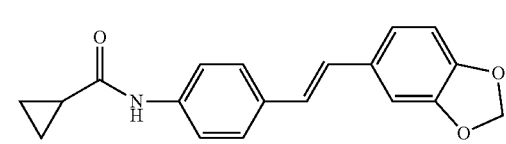

(iv)

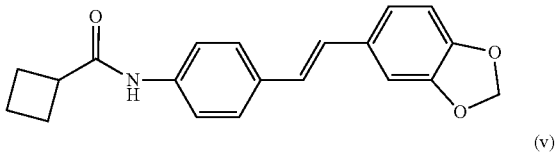

(v)

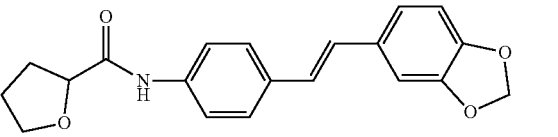

(vi)

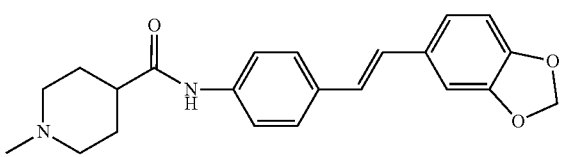

when the anhydride is acetic anhydride, propionic anhydride, n-butyric anhydride, isobutyric anhydride, benzoic anhydride, or di-tert-butyl dicarbonate, the structural formula of the compound is any of the following vii-xii:

(vii)

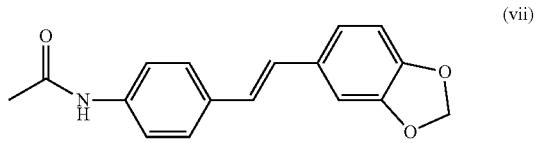

(viii)

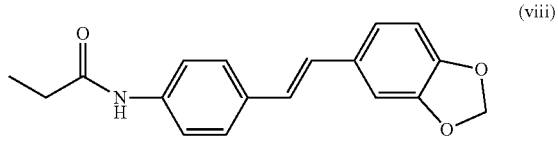

(ix)

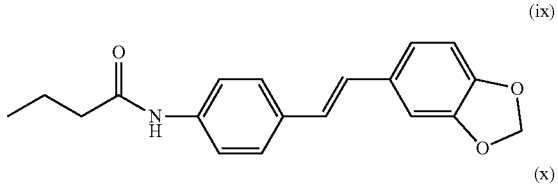

(x)

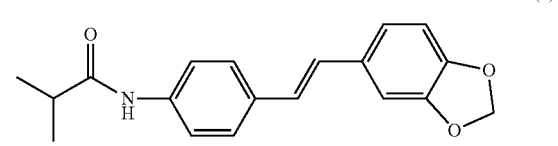

(xi)

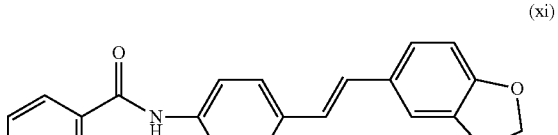

(xii)

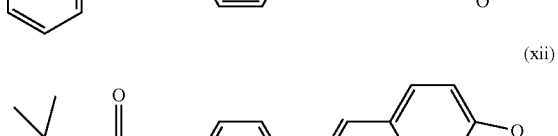

when the acyl chloride is p-toluenesulfonyl chloride, N,N-dimethylcarbamoyl chloride, benzenesulfonyl chloride, pivaloyl chloride, cyclopropylsulfonyl chloride, isopropylsulfonyl chloride, 4-methoxybenzoyl chloride, 4-cyanobenzoyl chloride, 4-chlorobenzenesulfonyl chloride, phenylacetyl chloride, benzylsulfonyl chloride, isopropyl chloroformate, dimethylaminosulfonyl chloride or 4-dimethylaminobenzoyl chloride, the structural formula of the compound is any of the following xiii-xxvi:

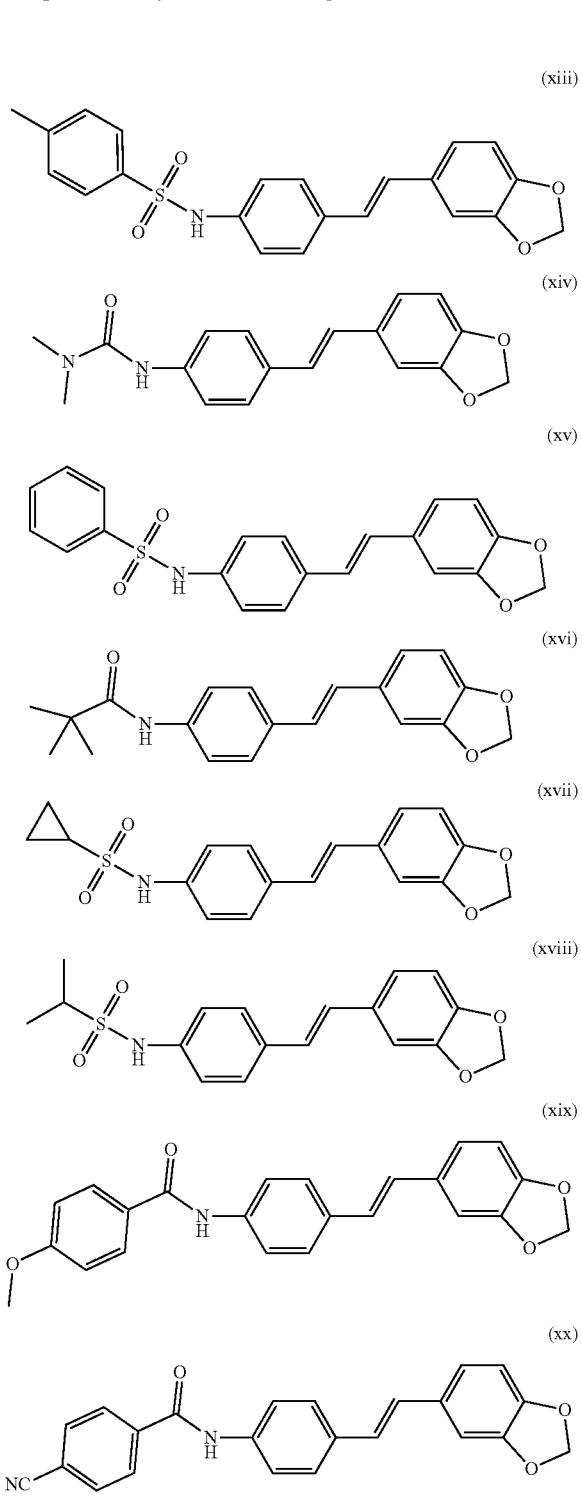

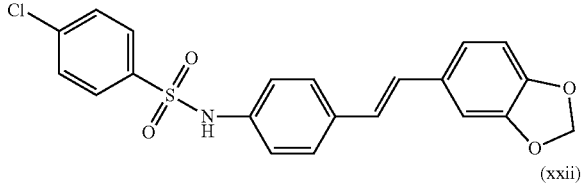

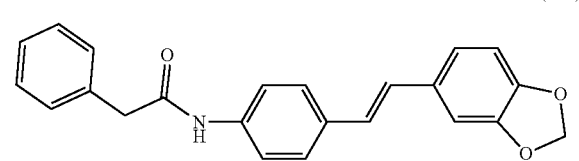

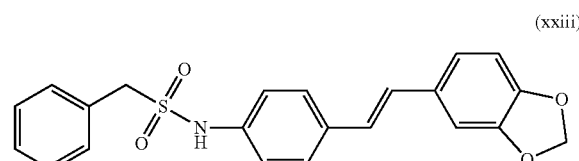

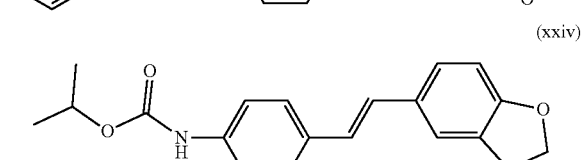

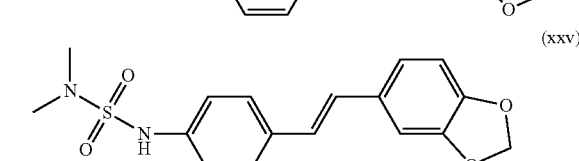

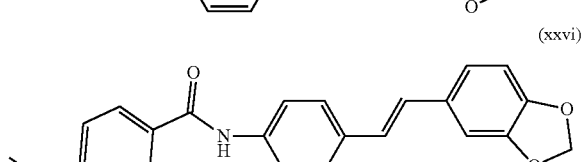

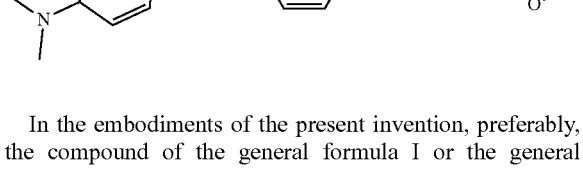

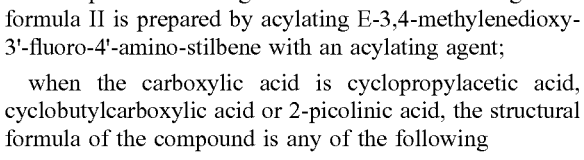

In the embodiments of the present invention, preferably, the compound of the general formula I or the general formula II is prepared by acylating E-3,4-methylenedioxy-3'-fluoro-4'-amino-stilbene with an acylating agent;

when the carboxylic acid is cyclopropylacetic acid, cyclobutylcarboxylic acid or 2-picolinic acid, the structural formula of the compound is any of the following

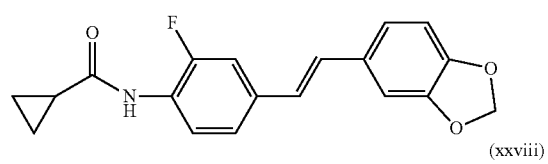

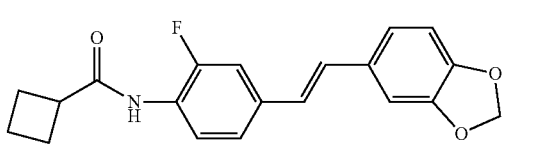

(xxix)

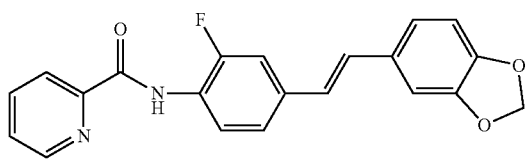

when the anhydride is acetic anhydride, isobutyric anhydride or benzoic anhydride, the structural formula of the compound is any of the following xxx-xxxii:

(xxx)

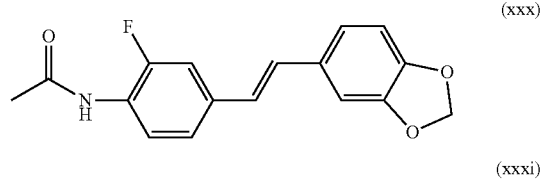

(xxxi)

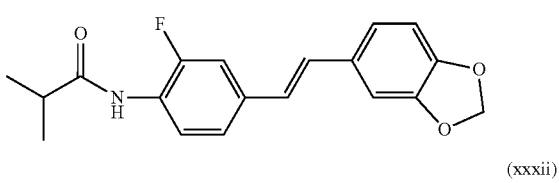

(xxxii)

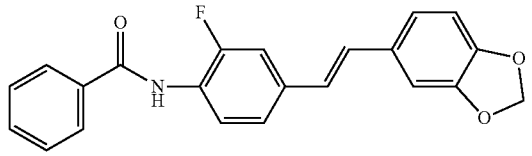

When the acyl chloride is N,N-dimethylcarbamoyl chloride, methylsulfonyl chloride, cyclopropylsulfonyl chloride, isopropylsulfonyl chloride, dimethylsulfamoyl chloride, or benzenesulfonyl chloride, the structural formula of the compound is any of the following xxxiii-xxxviii:

(xxxiii)

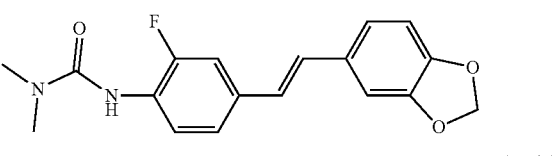

(xxxiv)

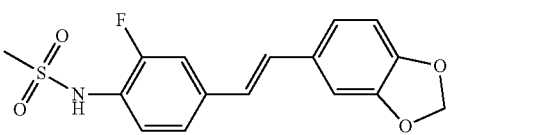

(xxxv)

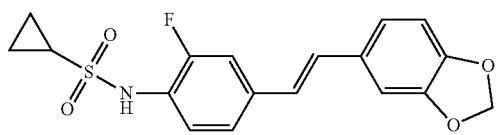

(xxxvi)

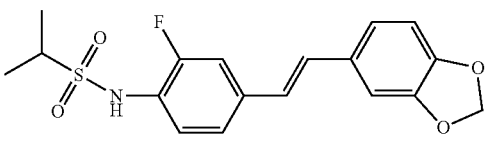

(xxxvii)

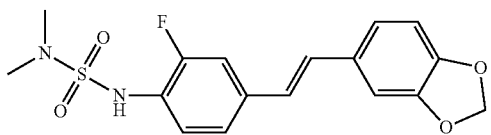

(xxxviii)

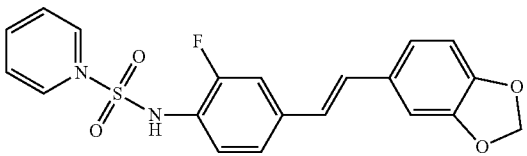

In the embodiments of the present invention, preferably, the compound of the general formula I or the general formula II is prepared by acylating E-4'-amino-3,4-methylenedioxy-stilbene with an acylating agent;

when the acylating agent is an acryloyl chloride, the structural formula of the compound is:

(xxxix)

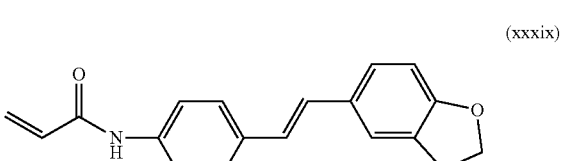

When the acylating agent is a cyclopentylcarboxylic acid, the structural formula of the compound is:

(xl)

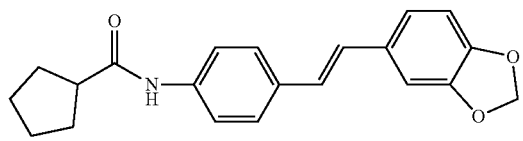

the compound of the general formula I or the general formula II is prepared by acylating E-3,4-methylenedioxy-3'-fluoro-4'-amino-stilbene with an acylating agent;

when the acylating agent is an acryloyl chloride, the structural formula of the compound is:

(xli)

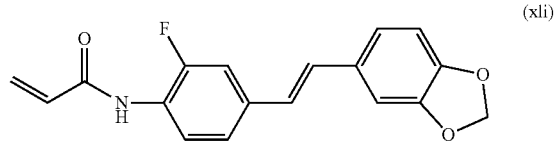 [SMILES: C=CC(=O)Nc1ccc(/C=C/c2ccc3c(c2)OCO3)cc1F]

when the acylating agent is a cyclopentylcarboxylic acid, the structural formula of the compound is:

(xlii)
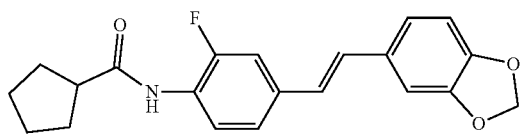

In the embodiments of the present invention, preferably, the compound of the general formula I or the general formula II is prepared by acylating the E-4'-amino-3,4-methylenedioxy-stilbene with the acylating agent;

when the carboxylic acid is a p-fluorophenylacrylic acid, p-cyanophenylacrylic acid or pyridylacrylic acid, the structural formula of the compound is any of the following xliii-xlv:

(xliii)
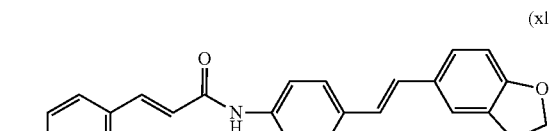

(xliv)
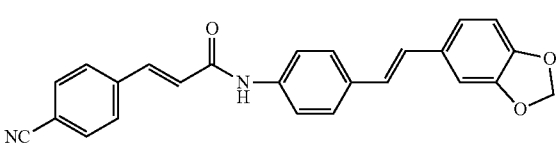

(xlv)
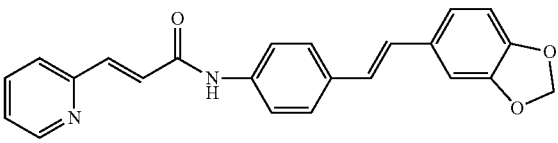

When the acyl chloride is a 3,3-dimethylacryloyl chloride, cinnamoyl chloride, p-tolylacryloyl chloride or p-chlorophenylacryloyl chloride, the structural formula of the compound is any of the following xlvi-xlix:

(xlvi)
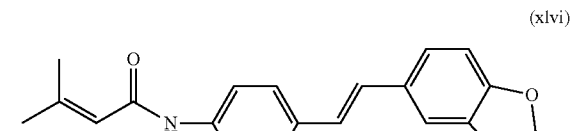

(xlvii)
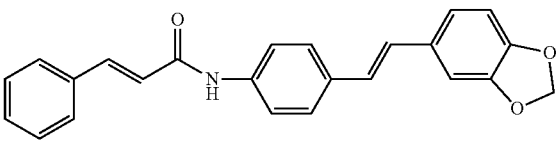

(xlviii)
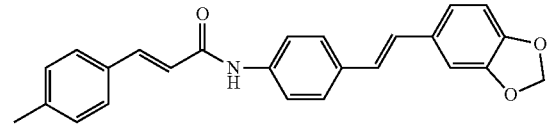

(xlix)
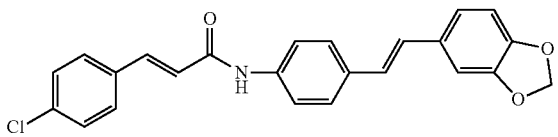

the compound of the general formula I or the general formula II is prepared by acylating E-3,4-methylenedioxy-3'-fluoro-4'-amino-stilbene with an acylating agent;

when the acyl chloride is a cinnamoyl chloride, the structural formula of the compound is:

(I)
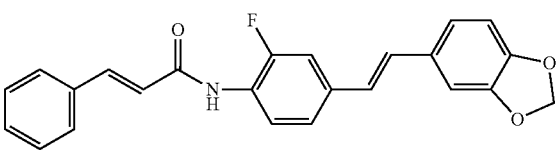

In the embodiments of the present invention, preferably, the inorganic acid is hydrochloric acid, sulfuric acid, hydrobromic acid, hydroiodic acid or phosphoric acid;

the organic acid is acetic acid, malonic acid, methanesulfonic acid, succinic acid, p-toluenesulfonic acid, citric acid, maleic acid or tartaric acid.

The present invention can further provide a pharmaceutical composition having neurogenesis activity and low neuronal cytotoxicity. The composition may comprise a compound of the foregoing general formulas, or a pharmaceutically acceptable salt and a pharmaceutically acceptable carrier formed from the compound of the foregoing general formulas. The present invention also relates to a pro-drug of the compound of the present invention, which is administered in a certain unpublished structure but metabolized or converted in the human body to the compound disclosed in the present invention and exert pharmacological effects as a pharmacologically effective component. For the present invention, various pharmaceutically acceptable acids can form salts on the heteroatom-nitrogen contained in the R groups in the general formula I and the general formula II, such as on the nitrogen atom of a tertiary aminophenyl, on the nitrogen atom of a methylpiperidine, on the nitrogen atom of dimethylamino, and on the nitrogen atom of pyridyl. Conventional methods for the preparation of the pro-drug are found in the "Design of Pro-drugs" (H. Bundgaad, Elsevier, 1985).

The invention further discloses a preparation method of the above novel stilbene derivative and specifically the preparation method of the compound of the general formula I or the general formula II comprises:

preparation of a crude compound: dissolving a reaction substrate in dichloromethane and adding a catalyst to obtain a mixture, and adding an acylating agent or a treated acylating agent dropwise to the mixture and stirring until the end of the reaction, and evaporating the dichloromethane off to obtain the crude compound, wherein the reaction substrate is E-4'-amino-3,4-methylenedioxystilbene or E-3,4-methylenedioxy-3'-fluoro-4'-amino-stilbene; and preparation of a compound: adding a saturated $NaHCO_3$ solution to the crude compound, adding dichloromethane for extraction to obtain an organic phase at the bottom, washing the organic phase with distilled water and saturated brine in turn, and concentrating by rotary evaporation and drying the washed organic phase to obtain a solid substance, and then carrying out column chromatography on the resulting solid substance to obtain a compound having neurogenesis activity and low neuronal cytotoxicity.

In an embodiment of the present invention, preferably, when the acylating agent is an anhydride or acyl chloride, the preparation method of the crude compound comprises:

dissolving the reaction substrate in dichloromethane, adding pyridine and 4-dimethylaminopyridine to obtain a mixture, and cooling the mixture in a cold water bath to below 0° C., adding the acylating agent dropwise to the mixture that is always lower than 0° C. and stirring until the end of the reaction, and evaporating the dichloromethane off to obtain the crude compound;

In an embodiment of the present invention, preferably, when the acylating agent is an acid, the preparation method of the crude compound comprises:

dissolving the acylating reagent in dichloromethane, adding triethylamine, stirring and dissolving, then adding pivaloyl chloride and stirring to dissolve the pivaloyl chloride to obtain the treated acylating reagent; and dissolving the reaction substrate in dichloromethane, and adding the treated acylating agent dropwise, resting at room temperature until the end of the reaction, and evaporating the dichloromethane off to obtain the crude compound.

In an embodiment of the present invention, preferably, the method further comprises:

preparation of an acceptable salt: adding an inorganic or organic acid to the resulting compound to obtain an acceptable novel stilbene derivative with neurogenesis activity and low neuronal cytotoxicity.

Correspondingly, the present invention further provides a preparation method of the above-mentioned novel stilbene derivative, which specifically refers to the following embodiments.

Reference is made to FIG. 1 which illustrates a flow chart of a preparation method of a novel stilbene derivative according to an embodiment of the present invention. The novel stilbene derivative is a compound of the following general formula I or general formula II. The preparation method of the novel stilbene derivative may specifically comprise the following steps:

Step 101, a reaction substrate is dissolved in anhydrous dichloromethane, and then pyridine and 4-dimethylaminopyridine are added to obtain a mixture; the mixture is then cooled in a cold water bath to below 0° C.; an acylating agent is added drop by drop to the mixture that is always lower than 0° C. and stirred until the end of the reaction. The reaction substrate herein is E-4'-amino-3,4-methylenedioxy-diphenylethlene or E-3,4-methylenedioxy-3'-fluoro-4'-amino-diphenylethlene.

Step 102, a saturated NaHCO₃ solution is added and dichloromethane is added additionally for extraction to obtain an organic phase at the bottom; the organic phase is then washed with distilled water and saturated brine in turn, and the washed organic phase is concentrated by rotary evaporation and dried to obtain a solid substance; and column chromatography is carried out on the resulting solid substance to obtain a compound having neurogenesis activity and low neuronal cytotoxicity.

Here, the reaction substrates E-4'-amino-3,4-methylenedioxy-diphenylethlene and E-3,4-methylenedioxy-3'-fluoro-4'-amino-diphenylethlene are both known substances, and the preparation methods of the two substances are similar.

Taking E-4'-amino-3,4-methylenedioxy-diphenylethlene as an example, at least three preparation methods may be included, for example:

In the first method, after the Heck reaction between 4-nitrostyrene and 1-iodo-3,4-methylenedioxybenzene, reduction (for example, with anhydrous SnCl₂) is carried out to obtain the E-4'-amino-3,4-methylenedioxy-diphenylethlene, and the reaction formula is as follows:

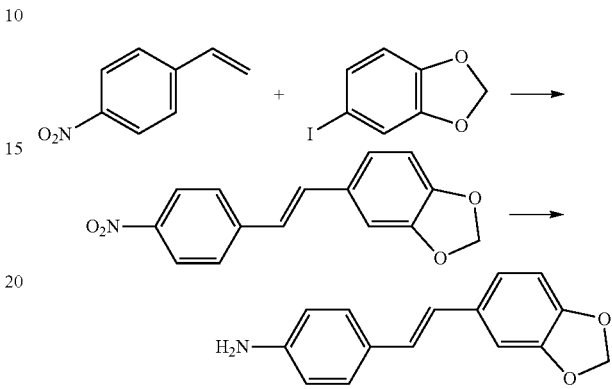

In the second method, the E-4'-amino-3,4-methylenedioxy-diphenylethlene is directly obtained through the Heck reaction between 4-aminostyrene and 1-iodo-3,4-methylenedioxybenzene, and the reaction formula is as follows:

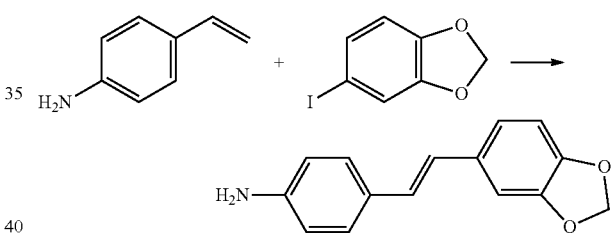

In the third method, with piperonal as a raw material, formyl is converted to ethylene (such as sodium amide and triphenylmethyl phosphonium bromide) to obtain 3,4-methylenedioxystyrene, and then the 3,4-methylenedioxystyrene has a Heck reaction with 1-iodine-4-nitrobenzene to obtain the E-4'-amino-3,4-methylenedioxy-diphenylethlene and the reaction formula is as follows:

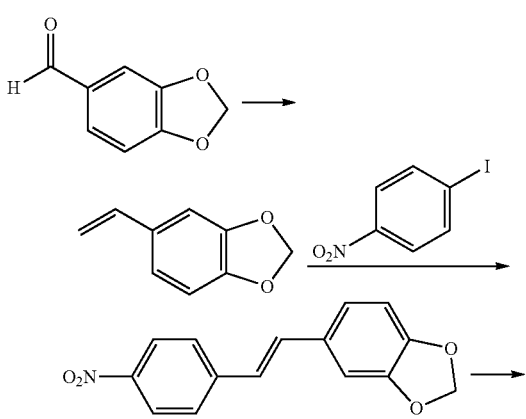

-continued

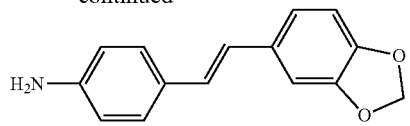

It should be noted that other methods for preparing E-4'-amino-3,4-methylenedioxy-diphenylethlene may also be included, which will not be described here.

Similarly, E-3,4-methylenedioxy-3'-fluoro-4'-amino-stilbene (WS-71b) may also be synthesized using the above methods.

The novel stilbene derivative of the general formula (I) or the general formula (II) prepared according to the methods of the embodiments of the present invention has a novel structure, and with the novel structure, the novel stilbene derivative has relatively good neurogenesis activity and low neuronal cytotoxicity, the neurogenesis activity, low cytotoxicity and other properties of the novel stilbene derivative can be further explained by test experiments and experimental data in subsequent examples.

Figure 2:
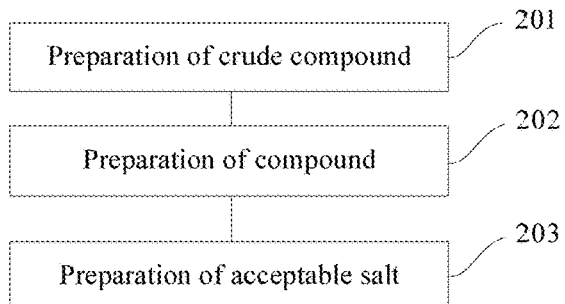
FIG. 2 is a flow chart of a preparation method of a novel stilbene derivative according to Embodiment 2 of the present invention.

Reference is made to FIG. 2 which illustrates a flow chart of a preparation method of a novel stilbene derivative according to Embodiment 2 of the present invention. The novel stilbene derivative is an acceptable salt formed by the compound of the general formula I or the general formula II and an inorganic acid or an organic acid. The preparation method of the novel stilbene derivative may comprise of the following steps:

Step 201, a reaction substrate is dissolved in anhydrous dichloromethane, and then pyridine and 4-dimethylaminopyridine are added to obtain a mixture; the mixture is then cooled in a cold water bath to below 0° C.; an acylating agent is added dropwise to the mixture that is always lower than 0° C. and stirred until the end of the reaction. The reaction substrate herein is E-4'-amino-3,4-methylenedioxy-diphenylethlene or E-3,4-methylenedioxy-3'-fluoro-4'-amino-diphenylethlene.

Step 202, a saturated NaHCO₃ solution is added and dichloromethane is added additionally for extraction to obtain an organic phase at the bottom; the organic phase is then washed with distilled water and saturated brine in turn, and the washed organic phase is concentrated by rotary evaporation and dried to obtain a solid substance; and column chromatography is carried out on the resulting solid substance to obtain a compound having neurogenesis activity and low neuronal cytotoxicity.

Step 203, an inorganic acid or organic acid is added to the resulting compound to generate a novel stilbene derivative having neurogenesis activity and low neuronal cytotoxicity.

In order to enable those skilled in the art to better understand the present invention, the preparation methods of E-4-amino-3',4'-methylenedioxy-stilbene, E-3,4-methylenedioxy-3'-fluoro-4'-amino-diphenylethlene, and the compound of the general formula I or the general formula II will be illustrated below by specific examples.

Example 1: The Reaction Formula for Preparing E-4-amino-3',4'-methylenedioxy-stilbene (WS-4) is

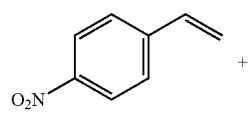

+

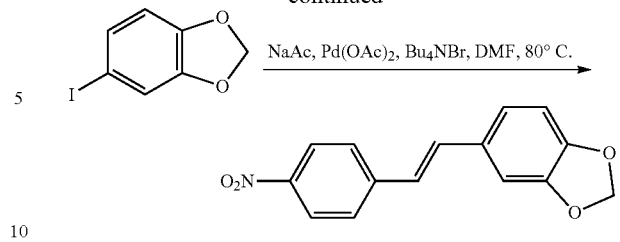

Specific steps may include the following: 3,4-methylenedioxy-iodobenzene (6.63 mmol, 1.644 g) is dissolved in DMF (60 mL) and then tetrabutylammonium bromide (3.33 mmol, 1.10 g), sodium acetate (3.57 mmol, 0.586 g), palladium acetate (0.11 mmol, 0.025 g) and 4-nitro-styrene (2.44 mmol, 0.365 g) are added. The reaction system is replaced with argon 5 times and stirred under the protection of argon for 5 h at 80° C. At the end of the reaction, distilled water (60 mL) is added to terminate the reaction, and then extraction is performed with ethyl acetate (75 mL); the organic phase at the top is washed with water (60 mL), and then washed with saturated brine (75 mL), concentrated by rotary evaporation, and dried to obtain a solid substance. The solid substance is dissolved in absolute ethanol (45 mL), then added with stannous chloride (33.15 mmol, 6.261 g) and stirred at reflux for 4 h. At the end of the reaction, ethanol is evaporated off, 1 mol/L NaOH (60 mL) is added, stirred for 0.5 h, extracted with ethyl acetate (75 mL), and the upper organic phase is washed with water (60 mL) and then washed with saturated brine (75 mL), concentrated by rotary evaporation, and dried to a solid substance. The solid substance is subjected to column chromatography (200-400-mesh silica gel, mobile phase being subject to V (dichloromethane): V (methanol)=10:0.1) to obtain a faint yellow powdered solid compound WS-4 (0.995 g, yield 62.7%).

HRMS (ESI) (M+H)+ m/z 240.10194, calcd for $C_{15}H_{14}NO_2$ 240.10191. $^1$H NMR (CDCl$_3$, 500 MHz) δ: 7.29-7.23 (m, 2H), 7.01 (d, J=1.5 Hz, 1H), 6.88-6.75 (m, 4H), 6.65-6.63 (m, 2H), 5.93 (s, 2H), 3.69 (s, 2H). $^{13}$C NMR (CDCl$_3$, 125 MHz) δ: 148.0, 146.7, 145.9, 132.5, 128.1, 127.5, 127.1, 124.8, 120.7, 115.2, 108.3, 105.3, 100.9.

Example 2: The Reaction Formula for Preparing E-4-acetylamino-3',4'-methylenedioxy-stilbene (WS-6) is

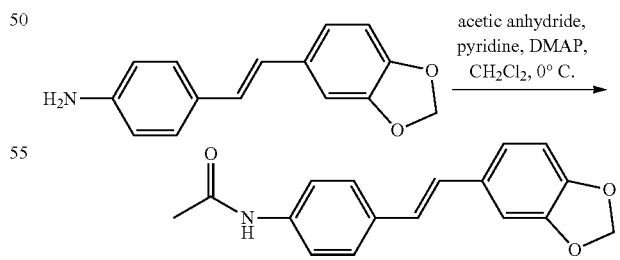

The specific steps may include the following: the compound WS-4 (2.22 mmol, 0.532 g) is added to a 100 mL round-bottom flask and dissolved with anhydrous dichloromethane (20 mL) while being stirred; pyridine (6.66 mmol, 0.518 g) and DMAP (0.22 mmol, 0.027 g) are added and then the solution is cooled to below 0° C. in an ice-water bath; acetic anhydride (6.66 mmol, 0.626 mL) is slowly added drop by drop, and during the addition, the temperature is always held below 0° C.; and the solution is then stirred to react in an ice-water bath for 0.5 h. At the end of the reaction, a saturated NaHCO₃ solution (25 mL) is added and stirred for 0.5 h. Additional 10 mL of dichloromethane is added for extraction, and the organic layer at the bottom is washed with water (20 mL), and then washed with saturated brine (25 mL), concentrated by rotary evaporation, and dried to obtain a solid substance. The solid substance is subjected to column chromatography (200-400-mesh silica gel, mobile phase being subject to V (dichloromethane): V (methanol)=10:0.1) to obtain a faint yellow powdered solid compound WS-6 (0.162 g, yield 26.0%).

HRMS (ESI) (M+H)+ m/z 282.11254, calcd for $C_{17}H_{16}NO_3$ 282.11247. ¹H NMR (Acetone-D6, 500 MHz) δ: 7.65 (d, J=8.5 Hz, 2H), 7.49-7.48 (m, 2H), 7.17 (d, J=1.5 Hz, 1H), 7.08 (d, J=16.5 Hz, 1H), 7.04 (d, J=16.0 Hz, 1H), 7.02-7.00 (m, 1H), 6.83 (d, J=8.0 Hz, 1H), 6.00 (s, 2H), 3.18 (s, 3H). ¹³C NMR (Acetone-D6, 125 MHz) δ: 169.2, 149.1, 148.1, 139.6, 133.6, 133.2, 127.8, 127.5, 127.3, 122.2, 120.1, 109.1, 106.0, 102.1, 24.1.

Example 3: The Reaction Formula for Preparing E-4-propionylamino-3',4'-methylenedioxy-stilbene (WS-40) is

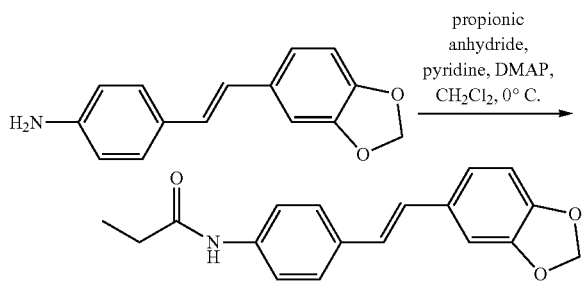

The specific steps may include the following: the compound WS-4 (2.00 mmol, 0.478 g) is added to a 100 mL round-bottom flask and dissolved with anhydrous dichloromethane (20 mL) while being stirred; pyridine (6.00 mmol, 0.475 g) and DMAP (0.20 mmol, 0.027 g) are added and then the solution is cooled to below 0° C. in an ice-water bath; propionic anhydride (6.00 mmol, 0.769 mL) is slowly added drop by drop, and during the addition, the temperature is always held below 0° C.; the solution is then stirred to react in an ice-water bath for 0.5 h. At the end of the reaction, a saturated NaHCO₃ solution (25 mL) is added and stirred for 0.5 h. Additional 20 mL of dichloromethane is added for extraction, and the organic layer at the bottom is washed with water (20 mL), and then washed with saturated brine (25 mL), concentrated by rotary evaporation, and dried to obtain a solid substance. The solid substance is subjected to column chromatography (200-400-mesh silica gel, mobile phase being subject to V (dichloromethane): V (methanol)=10:0.1) to obtain a faint yellow powdered solid compound WS-40 (0.486 g, yield 82.3%).

HRMS (ESI) (M+H)+ m/z 296.1284, calcd for $C_{18}H_{18}NO_3$ 296.1281. ¹H NMR (CDCl₃, 500 MHz) δ: 7.50 (d, J=8.0 Hz, 2H), 7.42 (d, J=8.5 Hz, 2H), 7.16 (s, 1H), 7.04 (d, J=1.5 Hz, 1H), 6.95 (d, J=16.5 Hz, 1H), 6.92 (dd, J=8.5, 2.0 Hz, 1H), 6.88 (d, J=16.0 Hz, 1H), 6.78 (d, J=8.0 Hz, 1H), 5.97 (s, 2H), 2.40 (q, J=7.5 Hz, 2H), 1.26 (t, J=7.5 Hz, 3H). ¹³C NMR (CDCl3, 125 MHz) δ: 171.8, 148.2, 147.2, 137.2, 133.5, 132.0, 127.6, 126.9, 126.4, 121.3, 119.8, 108.4, 105.5, 101.1, 30.8, 9.6.

Example 4: The Reaction Formula for Preparing E-4-butyrylamino-3',4'-methylenedioxy-stilbene (WS-50) is

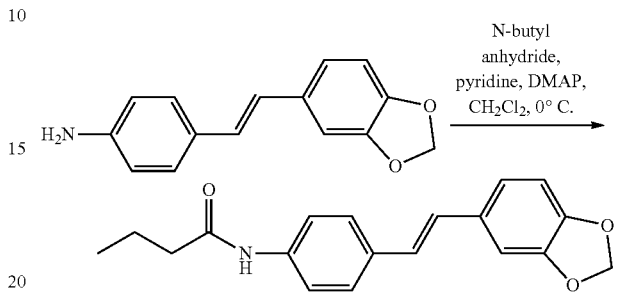

The specific steps may include the following: the compound WS-4 (2.48 mmol, 0.593 g) is added to a 100 mL round-bottom flask and dissolved with anhydrous dichloromethane (20 mL) while being stirred; pyridine (7.44 mmol, 0.579 g) and DMAP (0.25 mmol, 0.031 g) are added and then the solution is cooled to below 0° C. in an ice-water bath; n-butanoic anhydride (7.44 mmol, 0.699 mL) is slowly added dropwise, and during the addition, the temperature is always held below 0° C.; and the solution is then stirred to react in an ice-water bath for 0.5 h. At the end of the reaction, a saturated NaHCO₃ solution (25 mL) is added and stirred for 0.5 h. Additional 10 mL of dichloromethane is added for extraction, and the organic layer at the bottom is washed with water (20 mL), and then washed with saturated brine (25 mL), concentrated by rotary evaporation, and dried to obtain a solid substance. The solid substance is subjected to column chromatography (200-400-mesh silica gel, mobile phase being subject to V (petroleum ether): V (ethyl acetate)=10:3) to obtain a faint yellow powdered solid compound WS-50 (0.390 g, yield 50.7%).

HRMS (ESI) (M+H)+ m/z 310.1435, calcd for $C_{19}H_{20}NO_3$ 310.1438. ¹H NMR (CDCl₃, 500 MHz) δ: 7.50 (d, J=8.5 Hz, 2H), 7.42 (d, J=8.5 Hz, 2H), 7.18 (br, 1H), 7.04 (d, J=1.5 Hz, 1H), 6.95 (d, J=16.5 Hz, 1H), 6.92 (dd, J=8.0, 1.5 Hz, 1H), 6.88 (d, J=16.5 Hz, 1H), 6.78 (d, J=8.0 Hz, 1H), 5.96 (s, 2H), 2.34 (t, J=7.5 Hz, 2H), 1.81-1.73 (m, 2H), 1.02 (t, J=7.5 Hz, 3H). ¹³C NMR (CDCl₃, 125 MHz) δ: 171.0, 148.1, 147.2, 137.2, 133.4, 132.0, 127.6, 126.9, 126.4, 121.3, 119.8, 108.4, 105.5, 101.1, 39.7, 19.0, 13.7.

Example 5: The Reaction Formula for Preparing E-4-isobutyrylamino-3',4'-methylenedioxy-stilbene (WS-54) is

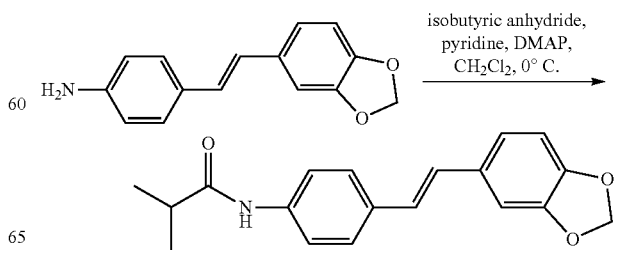

The specific steps may include the following: the compound WS-4 (4.00 mmol, 0.956 g) is added to a 100 mL round-bottom flask and dissolved with anhydrous dichloromethane (30 mL) while being stirred; pyridine (12.00 mmol, 0.933 g) and DMAP (0.40 mmol, 0.049 g) are added and then the solution is cooled to below 0° C. in an ice-water bath; isobutyric anhydride (12.00 mmol, 1.138 mL) is slowly added drop by drop, and during the addition, the temperature is always held below 0° C.; and the solution is then stirred to react in an ice-water bath for 0.5 h. At the end of the reaction, a saturated NaHCO$_3$ solution (35 mL) is added and stirred for 0.5 h. Additional 20 mL of dichloromethane is added for extraction, and the organic layer at the bottom is washed with water (30 mL), and then washed with saturated brine (35 mL), concentrated by rotary evaporation, and dried to obtain a solid substance. The solid substance is subjected to column chromatography (200-400-mesh silica gel, mobile phase being subject to V (dichloromethane): V (methanol)=10:0.1) to obtain a faint yellow powdered crude product WS-54 (0.303 g, yield 24.4%). The solid substance is subjected to column chromatography (200-400-mesh silica gel, mobile phase being subject to V (dichloromethane): V (methanol)=10:0.1) to obtain a white powdered solid compound WS-54 (0.115 g, yield 9.3%).

HRMS (ESI) (M+H)+ m/z 310.1438, calcd for C$_{19}$H$_{20}$NO$_3$ 310.1438. $^1$H NMR (CDCl$_3$, 500 MHz) δ: 7.52 (d, J=8.5 Hz, 2H), 7.44-7.42 (m, 2H), 7.13 (br, 1H), 7.04 (d, J=1.5 Hz, 1H), 6.95 (d, J=16.0 Hz, 1H), 6.92 (dd, J=8.0, 1.5 Hz, 1H), 6.88 (d, J=16.0 Hz, 1H), 6.79 (d, J=8.0 Hz, 1H), 5.97 (s, 2H), 2.55-2.47 (m, 1H), 1.27 (s, 3H), 1.26 (s, 3H). $^{13}$C NMR (CDCl$_3$, 125 MHz) δ: 175.0, 148.2, 147.2, 137.2, 133.5, 132.0, 127.6, 126.9, 126.4, 121.3, 119.8, 108.4, 105.5, 101.1, 36.8, 19.6.

Example 6: The Reaction Formula for Preparing E-4-methanesulfonylamino-3',4'-methylenedioxy-stilbene (WS-69) is

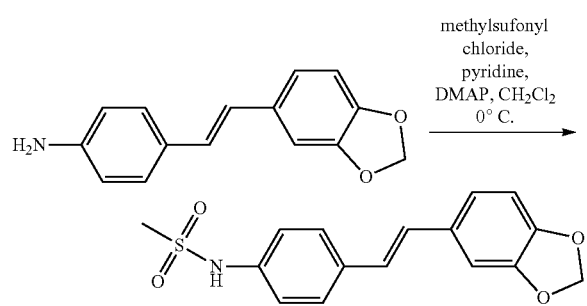

The specific steps may include the following: the compound WS-4 (1.60 mmol, 0.383 g) is added to a 100 mL round-bottom flask and dissolved with anhydrous dichloromethane (30 mL) while being stirred; pyridine (4.80 mmol, 0.379 g) and DMAP (0.16 mmol, 0.019 g) are added and then the solution is cooled to below 0° C. in an ice-water bath; methylsufonyl chloride (4.80 mmol, 0.371 mL) is slowly added drop by drop, and during the addition, the temperature is always held below 0° C.; and the solution is then stirred to react in an ice-water bath for 0.5 h. At the end of the reaction, the dichloromethane is evaporated off and then a saturated NaHCO$_3$ solution (25 mL) is added and stirred for 0.5 h. Additional 30 mL of dichloromethane is added for extraction, and the organic layer at the bottom is washed with water (20 mL), and then washed with saturated brine (25 mL), concentrated by rotary evaporation, and dried to obtain a solid substance. The solid substance is subjected to column chromatography (200-300-mesh silica gel, mobile phase being subject to V (dichloromethane): V (methanol)=10:0.5) to obtain a yellow powdered solid compound WS-69 (0.215 g, yield 42.4%).

HRMS (ESI) (M–H)– m/z 316.0661, calcd for C$_{16}$H$_{14}$NO$_4$S 316.0649. $^1$H NMR (Acetone-D6, 500 MHz) δ: 8.57 (s, 1H), 7.57-7.35 (m, 2H), 7.34-7.32 (m, 2H), 7.18 (d, J=1.5 Hz, 1H), 7.13 (d, J=16.5 Hz, 1H), 7.08 (d, J=16.5 Hz, 1H), 7.02 (dd, J=8.0, 1.5 Hz, 1H), 6.84 (d, J=8.0 Hz, 1H), 6.01 (s, 2H), 3.00 (s, 3H). $^{13}$C NMR (Acetone-D6, 125 MHz) δ: 149.3, 148.3, 138.6, 134.9, 133.0, 128.7, 128.2, 127.0, 122.4, 121.4, 109.1, 106.2, 102.2, 39.4.

Example 7: The Reaction Formula for Preparing E-4-benzoylamino-3',4'-methylenedioxy-stilbene (WS-70) is

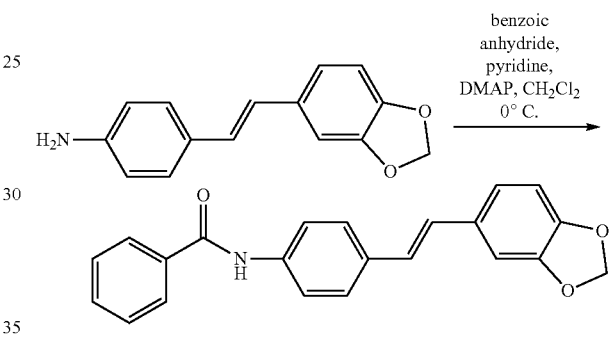

The specific steps may include the following: the compound WS-4 (0.89 mmol, 0.213 g) is added to a 100 mL round-bottom flask and dissolved with anhydrous dichloromethane (20 mL) while being stirred; pyridine (2.67 mmol, 0.211 g) and DMAP (0.089 mmol, 0.011 g) are added and then the solution is cooled to below 0° C. in an ice-water bath; benzoic anhydride (2.67 mmol, 0.604 mL) is slowly added, and during the addition, the temperature is always held below 0° C.; and the solution is then stirred to react in an ice-water bath for 0.5 h. At the end of the reaction, the dichloromethane is evaporated off and then a saturated NaHCO$_3$ solution (25 mL) is added and stirred for 0.5 h. Additional 20 mL of dichloromethane is added for extraction, and the organic layer at the bottom is washed with water (20 mL), and then washed with saturated brine (25 mL), concentrated by rotary evaporation, and dried to obtain a solid substance. The solid substance is subjected to column chromatography (200-300-mesh silica gel, mobile phase being subject to V (dichloromethane): V (methanol)=10:0.1) to obtain a faint yellow powdered crude compound (0.206 g, yield 67.5%). The crude compound is recrystallized with dichloromethane to obtain a white powdered solid compound WS-70 (0.120 g, yield 39.2%).

HRMS (ESI) (M+H)+ m/z 344.1274, calcd for C$_{22}$H$_{18}$NO$_3$ 344.1281. $^1$H NMR (DMSO-D6, 500 MHz) δ: 10.31 (s, 1H), 7.97-7.96 (m, 2H), 7.80 (d, J=8.5 Hz, 2H), 7.62-7.59 (m, 1H), 7.56-7.53 (m, 4H), 7.27 (d, J=1.5 Hz, 1H), 7.13 (d, J=16.0 Hz, 1H), 7.08 (d, J=16.5 Hz, 1H), 7.02 (dd, J=8.0, 1.5 Hz, 1H), 6.92 (d, J=8.0 Hz, 1H), 6.04 (s, 2H). $^{13}$C NMR (DMSO-D6, 125 MHz) δ: 165.4, 147.9, 146.8, 138.4, 134.9, 132.7, 131.8, 131.6, 128.4, 127.6, 127.0, 126.5, 126.3, 121.4, 120.4, 108.4, 105.2, 101.0.

Example 8: The Reaction Formula for Preparing E-3,4-Methylenedioxy-3'-fluoro-4'-amino-stilbene (WS-71b) is

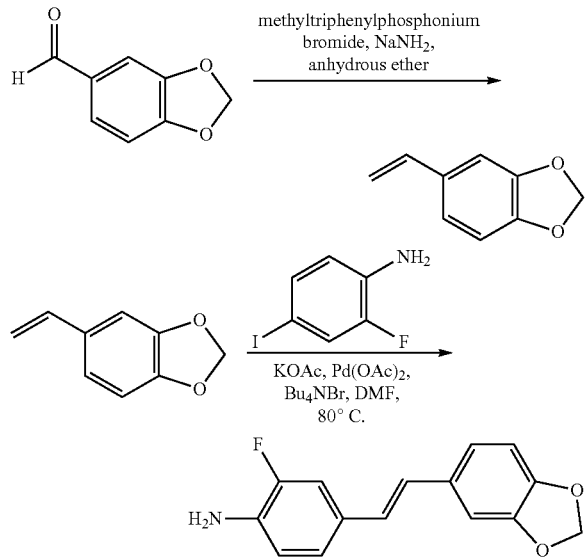

Specific steps may include the following: methyltriphenylphosphonium bromide (15.72 mmol, 5.58 g) and sodium amide (15.72 mmol, 0.60 g) are dissolved in anhydrous ether (50 mL) in the presence of argon; the solution is stirred at 25° C. for 7 h and then transferred to an environment with the temperature of −10° C.; 15 min later, piperonal (7.80 mmol, 1.20 g) dissolved in anhydrous ether (20 mL) is added dropwise; 15 min after all of the piperonal is added dropwise, the solution is transferring to an enthronement with the temperature of 25° C.; 15 h later, the ether is evaporated off and the residue is subjected to column chromatography (100-200-mesh silica gel, mobile phase being subject to V (petroleum ether): V (ethyl acetate)=10:3) to obtain a viscous, colorless and oily liquid WS-71a.

2-fluoro-4-iodoaniline (7.05 mmol, 1.670 g) is dissolved in DMF (40 mL) solution and tetrabutylammonium bromide (10.65 mmol, 3.519 g), potassium acetate (11.40 mmol, 1.119 g) was added, Palladium acetate (0.36 mmol, 0.075 g) and WS-71a are then added. The reaction system is replaced with argon 5 times and stirred under the protection of argon for 5 h at 80° C. At the end of the reaction, distilled water (30 mL) is added to terminate the reaction, and then extraction is performed with ethyl acetate (35 mL); the organic phase at the top is washed with water (20 mL), and then washed with saturated brine (25 mL), concentrated by rotary evaporation, and dried to obtain a solid substance. The solid substance is subjected to column chromatography (100-200-mesh silica gel, mobile phase being subject to V (petroleum ether): V (ethyl acetate)=10:3) to obtain a brownish yellow powdered solid WS-71b.

Example 9: The Reaction Formula for Preparing E-3,4-methylenedioxy-3'-fluoro-4'-acetylamino-stilbene (WS-71b) is

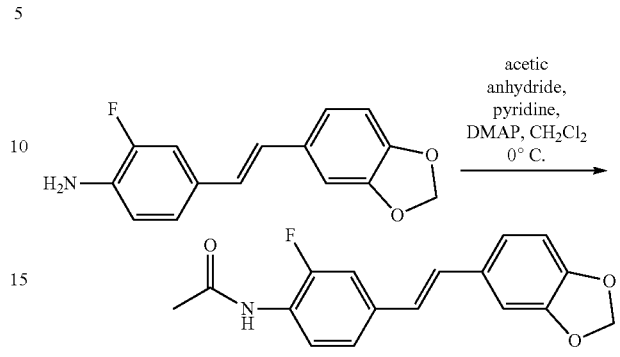

The specific steps may include the following: the compound WS-71b is added to a 100 mL round-bottom flask and dissolved with anhydrous dichloromethane (30 mL) while being stirred; pyridine (21.15 mmol, 1.645 g) and DMAP (0.705 mmol, 0.099 g) are added and then the solution is cooled to below 0° C. in an ice-water bath; acetic anhydride (21.15 mmol, 2.05 mL) is slowly added dropwise, and during the addition, the temperature is always held below 0° C.; and the solution is then stirred to react in an ice-water bath for 0.5 h. At the end of the reaction, the dichloromethane is evaporated off and then a saturated NaHCO₃ solution (30 mL) is added and stirred for 0.5 h. Additional 35 mL of dichloromethane is added for extraction, and the organic layer at the bottom is washed with water (20 mL), and then washed with saturated brine (25 mL), concentrated by rotary evaporation, and dried to obtain a solid substance. The solid substance is subjected to column chromatography (200-300-mesh silica gel, mobile phase being subject to V (dichloromethane): V (methanol)=10:0.1) to obtain a brownish yellow powdered solid compound WS-71 (0.511 g, yield 24.2%).

HRMS (ESI) (M+H+m/z 300.1028, calcd for $C_{17}H_{15}FNO_3$ 300.1030. $^1H$ NMR (Acetone-D6, 500 MHz) δ: 8.90 (s, 1H), 8.24-8.22 (m, 1H), 7.38-7.35 (m, 1H), 7.31 (d, J=8.5 Hz, 1H), 7.17 (d, J=1.5 Hz, 1H), 7.15 (d, J=16.0 Hz, 1H), 7.05 (d, J=16.0 Hz, 1H), 7.03 (dd, J=8.0, 1.5 Hz, 1H), 6.84 (d, J=8.0 Hz, 1H), 6.01 (s, 2H), 2.17 (s, 3H). $^{13}C$ NMR (Acetone-D6, 125 MHz) δ: 169.2, 149.3, 148.5, 135.3, 132.8, 129.5, 127.1, 127.0, 126.3, 126.3, 123.4, 123.4, 122.6, 112.9, 112.8, 109.2, 106.2, 102.2, 24.1.

Example 10: The Reaction Formula for Preparing E-4-(2-thienyl)formamino-3',4'-methylenedioxy-stilbene (WS-73) is

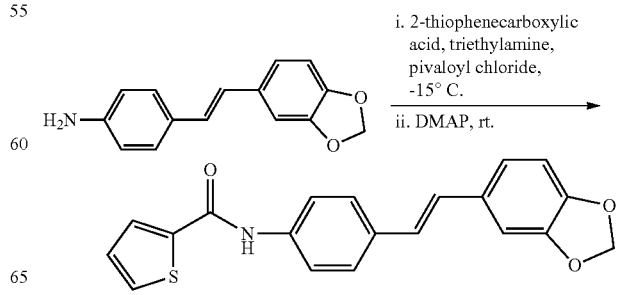

The specific steps may include the following: 2-thiophenecarboxylic acid (1.65 mmol, 0.211 g) is dissolved in dichloromethane (20 mL), and then triethylamine (1.65 mmol, 0.23 mL) is added and the solution is stirred at −15° C. for 15 min; then, pivaloyl chloride (1.65 mmol, 0.21 mL) is added dropwise and the solution is stirred at −15° C. for 0.5 h. WS-4 (0.5 mmol, 0.120 g) is dissolved in dichloromethane (20 mL) and added dropwise to the reaction system; then, DMAP (0.5 mmol, 0.061 g) is added; and the solution is transferred to an environment with room temperature to react for 4.5 h. At the end of the reaction, the dichloromethane is evaporated off and then a saturated $NaHCO_3$ solution (25 mL) is added and stirred for 0.5 h. Additional 20 mL of dichloromethane is added for extraction, and the organic layer at the bottom is washed with water (20 mL), and then washed with saturated brine (25 mL), concentrated by rotary evaporation, and dried to obtain a solid substance. The solid substance is subjected to column chromatography (200-300-mesh silica gel, mobile phase being dichloromethane) to obtain a faint yellow powdered crude compound (0.160 g, yield 91.7%). The crude compound is subjected to column chromatography (200-300-mesh silica gel, mobile phase being subject to V (petroleum ether): V (ethyl acetate)=1:1) again to obtain a faint yellow powdered compound WS-73 (0.118 g, yield 67.6%).

HRMS (ESI) (M+H)+ m/z 350.0844, calcd for $C_{20}H_{16}NO_3S$ 350.0773. $^1$H NMR (DMSO-D6, 500 MHz) δ: 10.26 (s, 1H), 8.03-8.02 (m, 1H), 7.85-7.84 (m, 1H), 7.74 (d, J=8.5 Hz, 2H), 7.54 (d, J=8.5 Hz, 2H), 7.26-7.22 (m, 2H), 7.12 (d, J=16.5 Hz, 1H), 7.07 (d, J=16.5 Hz, 1H), 7.01 (dd, J=8.0, 1.5 Hz, 1H), 6.90 (d, J=8.0 Hz, 1H), 6.03 (s, 2H). $^{13}$C NMR (DMSO-D6, 125 MHz) δ: 159.8, 147.9, 146.8, 140.4, 137.9, 132.8, 131.9, 131.8, 129.1, 128.1, 127.1, 126.6, 126.2, 121.4, 120.4, 108.4, 105.2, 101.0.

Example 11: the Reaction Formula for Preparing E-4-cyclopropylcarboxamino-3',4'-methylenedioxy-stilbene (WS-74) is

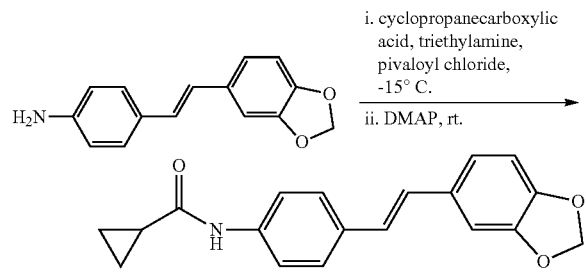

The specific steps may include the following: cyclopropanecarboxylic acid (1.65 mmol, 0.13 mL) is dissolved in dichloromethane (20 mL), and then triethylamine (1.65 mmol, 0.23 mL) is added and the solution is stirred at −15° C. for 15 min; then, pivaloyl chloride (1.65 mmol, 0.21 mL) is added drop by drop and the solution is stirred at −15° C. for 0.5 h. WS-4 (0.5 mmol, 0.120 g) is dissolved in dichloromethane (20 mL) and added drop by drop to the reaction system; then, DMAP (0.5 mmol, 0.061 g) is added; and the solution is transferred to an environment with room temperature to react for 3 h. At the end of the reaction, the dichloromethane is evaporated off and then a saturated $NaHCO_3$ solution (25 mL) is added and stirred for 0.5 h. Additional 20 mL of dichloromethane is added for extraction, and the organic layer at the bottom is washed with water (20 mL), and then washed with saturated brine (25 mL), concentrated by rotary evaporation, and dried to obtain a solid substance. The solid substance is subjected to column chromatography (200-300-mesh silica gel, mobile phase being subject to V (dichloromethane): V (methanol)=10:0.1) to obtain a faint yellow powdered compound WS-74 (0.112 g, yield 73.0%).

HRMS (ESI) (M+H)+ m/z 308.1282, calcd for $C_{19}H_{18}NO_3$ 308.1281. $^1$H NMR (DMSO-D6, 500 MHz) δ: 7.59 (d, J=9.0 Hz, 2H), 7.47 (d, J=8.5 Hz, 2H), 7.23 (d, J=1.0 Hz, 1H), 7.06 (d, J=16.5 Hz, 1H), 7.02 (d, J=16.5 Hz, 1H), 6.99 (dd, J=8.0, 1.5 Hz, 1H), 6.89 (d, J=7.5 Hz, 1H), 6.02 (s, 2H), 2.08-1.76 (m, 1H), 0.83-0.79 (m, 4H). $^{13}$C NMR (DMSO-D6, 125 MHz) δ: 171.5, 147.8, 146.7, 138.6, 132.0, 131.8, 126.7, 126.6, 126.3, 121.3, 119.0, 108.4, 105.1, 101.0, 14.6, 7.2.

Example 12: the Reaction Formula for Preparing E-4-(4-methylphenylsulfonamino)-3',4'-methylenedioxy-stilbene (WS-81) is

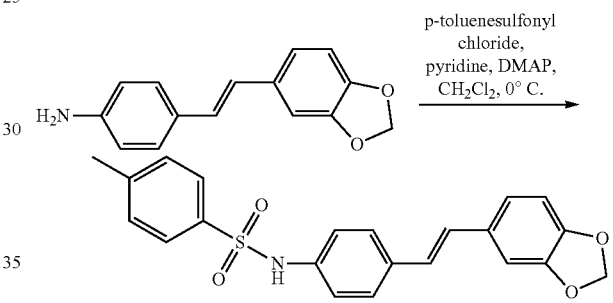

The specific steps may include the following: the compound WS-4 (1.06 mmol, 0.254 g) is added to a 100 mL round-bottom flask and dissolved with anhydrous dichloromethane (10 mL) while being stirred; pyridine (3.18 mmol, 0.252 g) and DMAP (0.11 mmol, 0.013 g) are added and then the solution is cooled to below 0° C. in an ice-water bath; p-toluenesulfonyl chloride (3.18 mmol, 0.606 mL) is slowly added drop by drop, and during the addition, the temperature is always held below 0° C.; and the solution is then stirred to react in an ice-water bath for 0.5 h. At the end of the reaction, the dichloromethane is evaporated off and then a saturated $NaHCO_3$ solution (25 mL) is added and stirred for 0.5 h. Additional 30 mL of dichloromethane is added for extraction, and the organic layer at the bottom is washed with water (20 mL), and then washed with saturated brine (25 mL), concentrated by rotary evaporation, and dried to obtain a solid substance. The solid substance is subjected to column chromatography (200-300-mesh silica gel, mobile phase being subject to V (dichloromethane): V (methanol) =10:0.5) to obtain a faint yellow powdered solid compound WS-81 (0.115 g, yield 27.6%).

$^1$H NMR (Acetone-D6, 500 MHz) δ: 8.96 (s, 1H), 7.69 (d, J=8.0 Hz, 2H), 7.43 (d, J=8.5 Hz, 2H), 7.31 (d, J=8.0 Hz, 2H), 7.21 (d, J=8.5 Hz, 2H), 7.13 (d, J=1.5 Hz, 1H), 7.06 (d, J=16.5 Hz, 1H), 6.99 (d, J=17.0 Hz, 1H), 6.98 (dd, J=8.0, 1.5 Hz, 1H), 6.81 (d, J=8.0 Hz, 1H), 5.99 (s, 2H), 2.35 (s, 3H). $^{13}$C NMR (Acetone-D6, 125 MHz) δ: 149.2, 148.3, 144.4, 138.1, 138.0, 134.9, 133.0, 130.4, 128.7, 128.0, 127.9, 126.9, 122.3, 121.8, 109.1, 106.1, 102.1, 21.4.

Example 13: Preparation of E-4-cyclobutylformamino-3',4'-methylenedioxy-stilbene (WS-83)

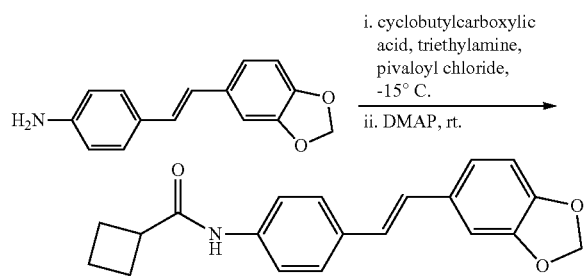

Cyclobutylcarboxylic acid (3.3 mmol, 0.30 mL) is dissolved in dichloromethane (20 mL), and then triethylamine (3.3 mmol, 0.46 mL) is added and the solution is stirred at −15° C. for 15 min; then, pivaloyl chloride (3.3 mmol, 0.42 mL) is added drop by drop and the solution is stirred at −15° C. for 0.5 h. WS-4 (1.0 mmol, 0.240 g) is dissolved in dichloromethane (20 mL) and added dropwise to the reaction system; then, DMAP (1.0 mmol, 0.122 g) is added; and the solution is transferred to an environment with room temperature to react for 3 h. At the end of the reaction, the dichloromethane is evaporated off and then a saturated NaHCO₃ solution (25 mL) is added and stirred for 0.5 h. Additional 20 mL of dichloromethane is added for extraction, and the organic layer at the bottom is washed with water (20 mL), and then washed with saturated brine (25 mL), concentrated by rotary evaporation, and dried to obtain a solid substance. The solid substance is subjected to column chromatography (200-300-mesh silica gel, mobile phase being subject to V (dichloromethane): V (methanol)=10:0.1) to obtain a white powdered compound WS-83 (0.068 g, yield 21.2%).

$^1$H NMR (Acetone-D6, 500 MHz) δ: 8.91 (s, 1H), 7.67 (d, J=8.5 Hz, 2H), 7.49-7.47 (m, 2H), 7.16 (d, J=1.5 Hz, 1H), 7.06-7.00 (m, 3H), 6.83 (d, J=8.0 Hz, 1H), 6.00 (s, 2H), 3.28-3.25 (m, 1H), 2.94-2.32 (m, 2H), 2.16-2.14 (m, 2H), 2.09-2.04 (m, 1H), 1.98-1.96 (m, 1H). $^{13}$C NMR (Acetone-D6, 125 MHz) δ: 173.6, 149.2, 148.2, 139.9, 133.5, 133.3, 127.8, 127.5, 127.4, 122.2, 120.2, 120.1, 109.1, 106.1, 102.1, 41.4, 25.7, 18.7.

Example 14: Preparation of E-4-(N,N-dimethylamino) formamino-3',4'-methylenedioxy-stilbene (WS-82)

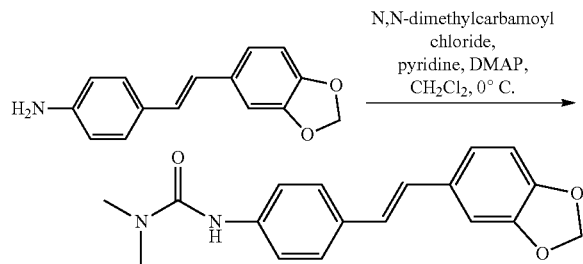

The compound WS-4 (1.00 mmol, 0.254 g) is added to a 100 mL round-bottom flask and dissolved with anhydrous dichloromethane (30 mL) while being stirred; pyridine (3.30 mmol, 0.3 mL) and DMAP (0.10 mmol, 0.012 g) are added and then the solution is cooled to below 0° C. in an ice-water bath; dimethylcarbamoyl chloride (3.3 mmol, 0.30 mL) is slowly added drop by drop, and during the addition, the temperature is always held below 0° C.; and the solution is then stirred to react in an ice-water bath for 0.5 h. At the end of the reaction, the dichloromethane is evaporated off and then a saturated NaHCO₃ solution (25 mL) is added and stirred for 0.5 h. Additional 30 mL of dichloromethane is added for extraction, and the organic layer at the bottom is washed with water (20 mL), and then washed with saturated brine (25 mL), concentrated by rotary evaporation, and dried to obtain a solid substance. The solid substance is subjected to column chromatography (200-300-mesh silica gel, mobile phase being subject to V (dichloromethane): V (methanol)=10:0.5) to obtain a white powdered solid compound WS-82 (0.213 g, yield 68.9%).

$^1$H NMR (Acetone-D6, 500 MHz) δ: 7.73 (s, 1H), 7.56-7.54 (m, 2H), 7.43-7.41 (m, 2H), 7.15 (d, J=2.0 Hz, 1H), 7.03-6.98 (m, 3H), 6.82 (d, J=8.5 Hz, 1H), 6.00 (s, 2H), 3.00 (s, 6H). $^{13}$C NMR (Acetone-D6, 125 MHz) δ: 156.4, 149.2, 148.0, 141.3, 133.4, 132.2, 127.7, 127.3, 127.0, 122.0, 120.3, 120.2, 109.1, 106.0, 102.1, 36.6.

Example 15: Preparation of E-4-benzenesulfonylamino-3',4'-methylenedioxy-stilbene (LSS-12)

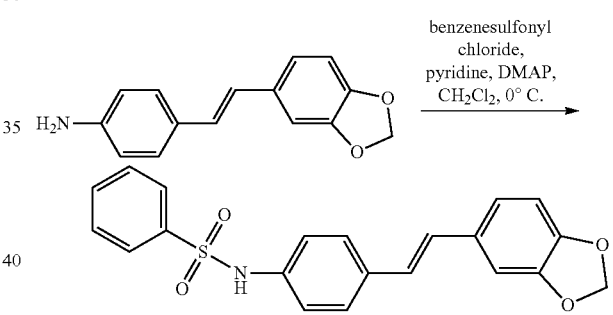

The compound WS-4 (1.2 mmol, 0.29 g) and DMAP (0.12 mmol, 0.015 g) are added to a 100 mL round-bottom flask and dissolved with anhydrous dichloromethane (20 mL) while being stirred; the solution is cooled to below 0° C. in an ice-water bath; pyridine (3.6 mmol, 0.3 mL) and benzenesulfonyl chloride (3.6 mmol, 0.46 mL) are slowly added dropwise, and during the addition, the temperature is always held below 0° C.; and the solution is then stirred to react in an ice-water bath for 1 h. At the end of the reaction, the dichloromethane is evaporated off and then a saturated NaHCO₃ solution (25 mL) is added and stirred for 0.5 h. Additional 30 mL of dichloromethane is added for extraction, and the organic layer at the bottom is washed with water (20 mL), and then washed with saturated brine (25 mL), concentrated by rotary evaporation, and dried to obtain a solid substance. The solid substance is subjected to column chromatography (200-300-mesh silica gel, mobile phase being V (dichloromethane) 100% to obtain a faint yellow powdered solid compound LSS-12 (0.197 g, yield 43.30%).

$^1$H NMR (DMSO-D6, 500 MHz) δ: 10.30 (s, 1H), 7.77 (d, J=7.0 Hz, 2H), 7.52-7.76 (m, 3H), 7.40 (d, J=8.5 Hz, 2H), 7.20 (s, 1H), 7.08 (d, J=8.5 Hz, 2H), 7.02 (d, J=16.0 Hz, 1H), 6.97 (d, J=16.0 Hz, 1H), 6.96 (d, J=8.0 Hz, 1H), 6.88 (d, J=8.0 Hz, 1H), 6.01 (s, 2H). $^{13}$C NMR (DMSO-D6, 125

MHz) δ: 149.2, 148.2, 140.9, 137.7, 135.1, 133.6, 132.9, 129.9, 128.7, 127.9, 126.8, 122.3, 122.0, 109.1, 106.1, 102.1.

Example 16: Preparation of E-4-pivalylamino-3',4'-methylenedioxy-stilbene (LSS-8)

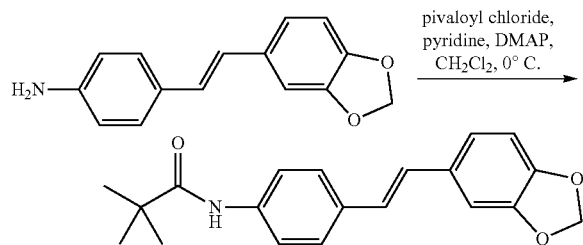

The compound WS-4 (1.2 mmol, 0.29 g) and DMAP (0.12 mmol, 0.015 g) are added to a 100 mL round-bottom flask and dissolved with anhydrous dichloromethane (20 mL); the solution is cooled to below 0° C. in an ice-water bath; pyridine (3.6 mmol, 0.3 mL) and pivaloyl chloride (3.6 mmol, 0.45 mL) are slowly added drop by drop to react in an ice-water bath for 1 h. At the end of the reaction, the dichloromethane is evaporated off and then a saturated NaHCO₃ solution (25 mL) is added and stirred for 0.5 h. Additional 30 mL of dichloromethane is added for extraction, and the organic layer at the bottom is washed with water (20 mL), and then washed with saturated brine (25 mL), concentrated by rotary evaporation, and dried to obtain a solid substance. The solid substance is subjected to column chromatography (200-300-mesh silica gel, mobile phase being subject to V (petroleum ether): V (acetone)=10:3) to obtain a faint yellow powdered solid compound LSS-8 (0.159 g, yield 40.97%).

$^1$H NMR (DMSO-D6, 500 MHz) δ: 9.21 (s, 1H), 7.68 (d, J=9.0 Hz, 2H), 7.47 (d, J=9.0 Hz, 2H), 7.23 (d, J=1.5 Hz, 1H), 7.08 (d, J=16.5 Hz, 1H), 7.03 (d, J=16.5 Hz, 1H), 6.99 (dd, J=8.0, 1.5 Hz, 1H), 6.88 (d, J=8.0 Hz, 1H), 6.02 (s, 2H), 1.24 (s, 9H). $^{13}$C NMR (DMSO-D6, 125 MHz) δ: 176.3, 147.8, 146.7, 138.6, 132.1, 131.8, 126.7, 126.3, 126.3, 121.2, 120.3, 108.3, 105.1, 100.9, 39.1, 27.1.

Example 17: Preparation of E-4-cyclopropylsulfonylamino-3',4'-methylenedioxy-stilbene (LSS-13)

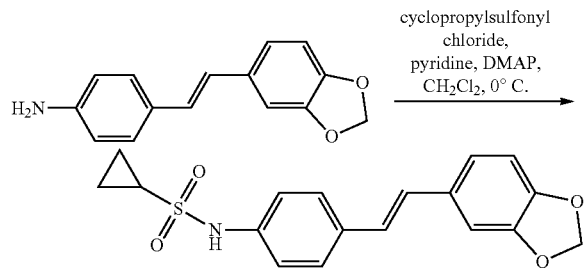

The compound WS-4 (0.84 mmol, 0.20 g) and DMAP (0.08 mmol, 0.01 g) are added to a 100 mL round-bottom flask and dissolved with anhydrous dichloromethane (20 mL); pyridine (2.52 mmol, 0.20 mL) and cyclopropylsulfonyl chloride (2.52 mmol, 0.25 mL) are added dropwise at room temperature to react at room temperature for 0.5 h. At the end of the reaction, the dichloromethane is evaporated off and then a saturated NaHCO₃ solution (25 mL) is added and stirred for 0.5 h. Additional 30 mL of dichloromethane is added for extraction, and the organic layer at the bottom is washed with water (20 mL), and then washed with saturated brine (25 mL), concentrated by rotary evaporation, and dried to obtain a solid substance. The solid substance is subjected to column chromatography (200-300-mesh silica gel, mobile phase being V (dichloromethane) 100% to obtain a faint yellow powdered solid compound LSS-13 (0.2436 g, yield 84.88%).

$^1$H NMR (DMSO-D6, 500 MHz) δ: 9.74 (s, 1H), 7.50 (d, J=8.5 Hz, 2H), 7.24 (dd, J=1.5 Hz, 1H), 7.23 (d, J=8.5 Hz, 2H), 7.08 (d, J=16.5 Hz, 1H), 7.05 (d, J=16.5 Hz, 1H), 7.00 (dd, J=8.0, 1.5 Hz, 1H), 6.89 (d, J=8.0 Hz, 1H), 6.02 (s, 2H), 2.60-2.64 (m, 1H), 0.92-0.94 (m, 4H). $^{13}$C NMR (DMSO-D6, 125 MHz) δ: 147.8, 146.8, 137.4, 133.0, 131.7, 127.3, 127.0, 126.0, 121.4, 120.4, 108.3, 105.2, 101.0, 29.6, 4.9.

Example 18: Preparation of E-4-isopropylsulfonamino-3',4'-methylenedioxy-stilbene (LSS-14)

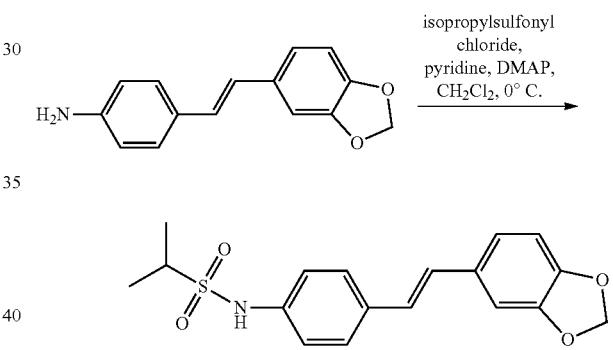

The compound WS-4 (1.25 mmol, 0.30 g) and DMAP (0.125 mmol, 0.015 g) are added to a 100 mL round-bottom flask and dissolved with anhydrous dichloromethane (20 mL); pyridine (3.75 mmol, 0.30 mL) and isopropylsulfonyl chloride (3.75 mmol, 0.45 mL) are added drop by drop at room temperature to react at room temperature for 6 days. At the end of the reaction, the dichloromethane is evaporated off and then a saturated NaHCO₃ solution (25 mL) is added and stirred for 0.5 h. Additional 30 mL of dichloromethane is added for extraction, and the organic layer at the bottom is washed with water (20 mL), and then washed with saturated brine (25 mL), concentrated by rotary evaporation, and dried to obtain a solid substance. The solid substance is subjected to column chromatography (200-300-mesh silica gel, mobile phase being subject to V (dichloromethane): V (methanol)=10:0.03) to obtain a faint yellow powdered solid compound LSS-14 (0.185 g, yield 42.73%).

$^1$H NMR (Acetone-D6, 500 MHz) δ: 7.51-7.54 (m, 2H), 7.35-7.38 (m, 2H), 7.16 (d, J=1.5 Hz, 1H), 7.10 (d, J=16.5 Hz, 1H), 7.05 (d, J=16.5 Hz, 1H), 7.00 (dd, J=8.5, 1.5 Hz, 1H), 6.82 (d, J=8.0 Hz, 1H), 6.00 (s, 2H), 3.27-3.33 (m, 1H), 1.34 (d, 3H), 1.31 (d, 3H). $^{13}$C NMR (Acetone-D6, 125 MHz) δ: 149.2, 148.2, 138.7, 134.4, 133.0, 128.4, 128.1, 126.9, 122.3, 120.7, 109.0, 106.1, 102.1, 52.8, 16.7.

Example 19: Preparation of E-4-(2-pyridinecarboxamino)-3',4'-methylenedioxy-stilbene (LSS-20)

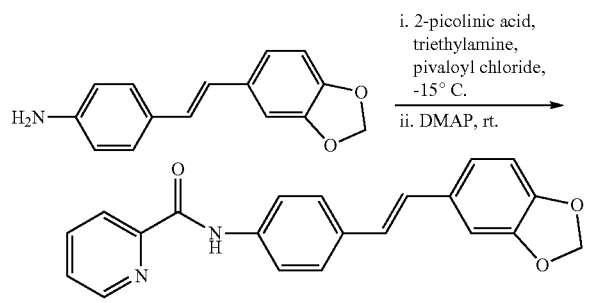

2-picolinic acid (3.3 mmol, 0.4 mL) is dissolved in dichloromethane (20 mL), and then triethylamine (3.3 mmol, 0.46 mL) is added and the solution is stirred at −15° C. for 15 min; then, pivaloyl chloride (3.3 mmol, 0.4 mL) is added dropwise and the solution is stirred at −15° C. for 3 h. WS-4 (1 mmol, 0.24 g) is dissolved in dichloromethane (20 mL) and added dropwise to the reaction system; then, DMAP (1 mmol, 0.13 g) is added; and the solution is transferred to an environment with room temperature to react for 1 h. At the end of the reaction, the dichloromethane is evaporated off and then a saturated NaHCO₃ solution (25 mL) is added and stirred for 0.5 h. Additional 20 mL of dichloromethane is added for extraction, and the organic layer at the bottom is washed with water (20 mL), and then washed with saturated brine (25 mL), concentrated by rotary evaporation, and dried to obtain a solid substance. The solid substance is subjected to column chromatography (200-300-mesh silica gel, mobile phase being dichloromethane) to obtain a faint yellow powdered crude compound. The crude compound is subjected to column chromatography (200-300-mesh silica gel, mobile phase being subject to V (petroleum ether): V (ethyl acetate)=10:3) again to obtain a faint yellow powdered compound LSS-20 (0.157 g, yield 45.71%).

¹H NMR (DMSO-D6, 500 MHz) δ: 10.55 (s, 1H), 8.64 (d, J=1.5 Hz, 1H), 8.06 (d, J=7.5 Hz, 1H), 7.96-7.99 (m, 1H), 7.82 (d, J=8.5 Hz, 2H), 7.57-7.59 (m, 1H), 7.45 (d, J=8.5 Hz, 2H), 7.15 (s, 1H), 7.03 (d, J=16.0 Hz, 1H), 6.98 (d, J=17.0 Hz, 1H), 6.91 (dd, J=1.0 Hz, J=8.0 Hz, 1H), 6.81 (d, J=7.5 Hz, 1H), 5.93 (s, 2H).

Example 20: Preparation of E-4-(tert-butoxycarbonylamino)-3',4'-methylenedioxy-stilbene (LSS-19)

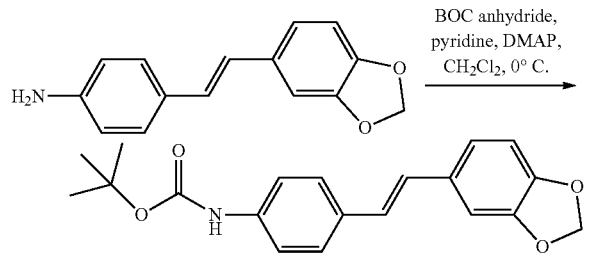

The compound WS-4 (0.83 mmol, 0.20 g) and DMAP (0.083 mmol, 0.01 g) are added to a 100 mL round-bottom flask and dissolved with anhydrous dichloromethane (20 mL); the solution is cooled to below 0° C. in an ice-water bath; pyridine (2.49 mmol, 0.2 mL) and BOC anhydride (2.49 mmol, 0.57 mL) are slowly added drop by drop to react at room temperature for 0.5 h. At the end of the reaction, the dichloromethane is evaporated off and then a saturated NaHCO₃ solution (25 mL) is added and stirred for 0.5 h. Additional 30 mL of dichloromethane is added for extraction, and the organic layer at the bottom is washed with water (20 mL), and then washed with saturated brine (25 mL), concentrated by rotary evaporation, and dried to obtain a solid substance. The solid substance is subjected to column chromatography (200-300-mesh silica gel, mobile phase being V (dichloromethane) 100% to obtain a faint yellow powdered solid compound LSS-19 (0.1995 g, yield 71.25%).

¹H NMR (DMSO-D6, 500 MHz) δ: 7.59-7.62 (m, 2H), 7.28-7.30 (m, 2H), 7.23 (d, J=1.5 Hz, 1H), 7.22 (d, J=16.5 Hz, 1H), 7.14 (d, J=16.5 Hz, 1H), 7.06 (dd, J=8.0, 1.5 Hz, 1H), 6.86 (d, J=8.0 Hz, 1H), 6.03 (s, 2H), 1.47 (s, 9H).

Example 21: Preparation of E-4-(4-methoxybenzamino)-3',4'-methylenedioxy-stilbene

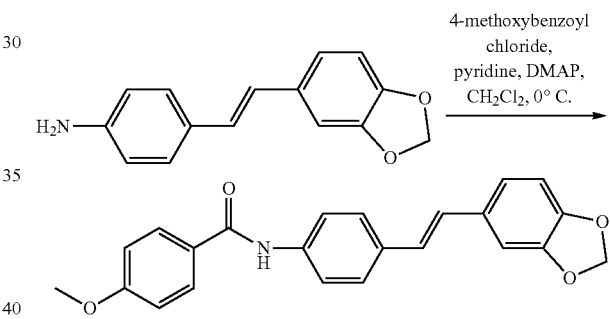

Using the method of Example 6, WS-4 reacts with 4-methoxybenzoyl chloride to obtain the above target compound.

Example 22: Preparation of E-4-(4-cyanobenzoylamino)-3',4'-methylenedioxy-stilbene

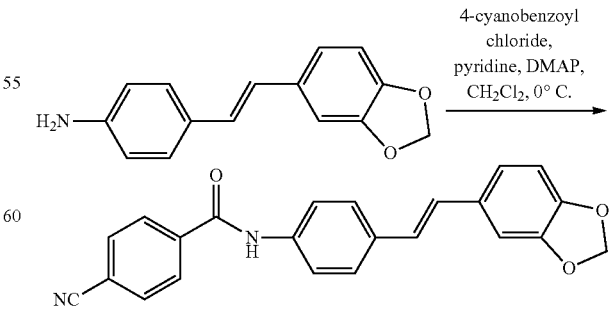

Using the method of Example 6, WS-4 reacts with 4-cyanobenzoyl chloride to obtain the above target compound.

Example 23: Preparation of E-4-(4-chlorophenylsulfonamino)-3',4'-methylenedioxy-stilbene

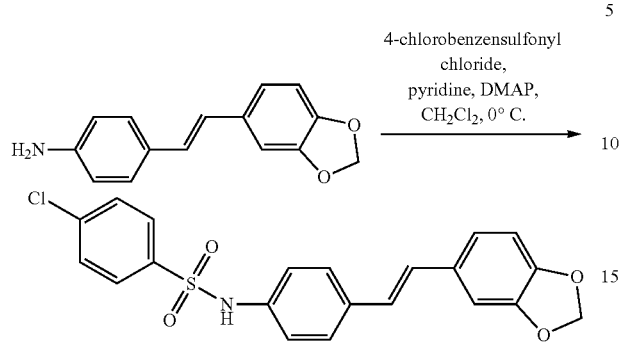

Using the method of Example 6, WS-4 reacts with 4-chlorobenzenesulfonyl chloride to obtain the above target compound.

Example 24: Preparation of E-4-phenylacetylamino-3',4'-methylenedioxy-stilbene (LSS-16)

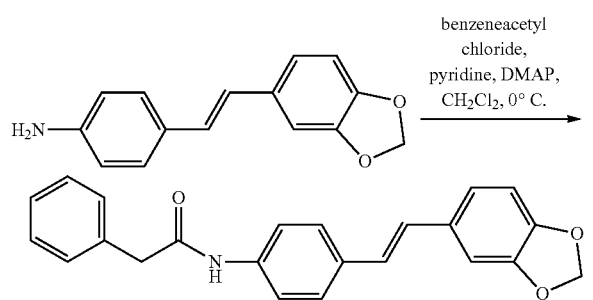

The compound WS-4 (1.17 mmol, 0.28 g) and DMAP (0.012 mmol, 0.014 g) are added to a 100 mL round-bottom flask and dissolved with anhydrous dichloromethane (20 mL); pyridine (3.51 mmol, 0.28 mL) and benzeneacetyl chloride (3.51 mmol, 0.46 mL) are added drop by drop at room temperature to react at room temperature for 1 h. At the end of the reaction, the dichloromethane is evaporated off and then a saturated $NaHCO_3$ solution (25 mL) is added and stirred for 0.5 h. Additional 30 mL of dichloromethane is added for extraction, and the organic layer at the bottom is washed with water (20 mL), and then washed with saturated brine (25 mL), concentrated by rotary evaporation, and dried to obtain a solid substance. The solid substance is subjected to column chromatography (200-300-mesh silica gel, mobile phase being subject to V (dichloromethane): V (methanol) =10:0.1) to obtain a faint yellow powdered solid compound LSS-16 (0.2782 g, yield 66.56%).

$^1$H NMR (Acetone-D6, 500 MHz) δ: 9.29 (s, 1H), 7.64-7.66 (m, 2H), 7.47-7.49 (m, 2H), 7.38-7.39 (m, 2H), 7.30-7.33 (m, 2H), 7.23-7.26 (m, 1H), 7.16 (d, J=1.5 Hz, 1H), 7.08 (d, J=16.5 Hz, 1H), 7.04 (d, J=16.5 Hz, 1H), 7.00 (dd, J=8.0, 1.5 Hz, 1H), 6.82 (d, J=8.0 Hz, 1H), 6.00 (s, 2H), 3.70 (s, 2H). $^{13}$C NMR (Acetone-D6, 125 MHz) δ: 169.7, 149.3, 148.2, 139.7, 136.9, 133.2, 130.1, 129.2, 128.0, 127.6, 127.5, 127.4, 122.2, 120.3, 120.2, 109.1, 106.1, 102.1, 44.8.

Example 25: Preparation of E-4-benzylsulfonylamino-3',4'-methylenedioxy-stilbene (LSS-15)

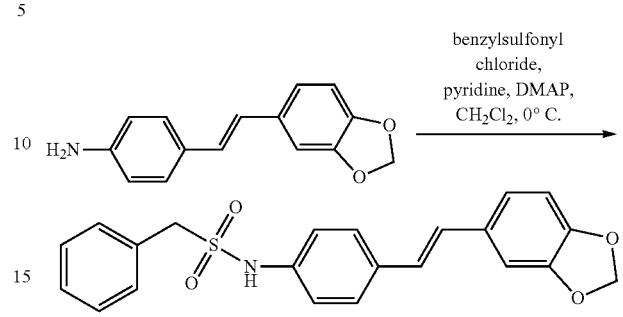

The compound WS-4 (1.25 mmol, 0.30 g) and DMAP (0.125 mmol, 0.015 g) are added to a 100 mL round-bottom flask and dissolved with anhydrous dichloromethane (20 mL); pyridine (3.75 mmol, 0.30 mL) and benzylsulfonyl chloride (3.75 mmol, 0.72 mL) are added dropwise at room temperature to react at room temperature for 3 h. At the end of the reaction, the dichloromethane is evaporated off and then a saturated $NaHCO_3$ solution (25 mL) is added and stirred for 0.5 h. Additional 30 mL of dichloromethane is added for extraction, and the organic layer at the bottom is washed with water (20 mL), and then washed with saturated brine (25 mL), concentrated by rotary evaporation, and dried to obtain a solid substance. The solid substance is subjected to column chromatography (200-300-mesh silica gel, mobile phase being subject to V (dichloromethane): V (methanol)=10:0.03) to obtain a faint yellow powdered solid compound LSS-15 (0.2869 g, yield 58.55%).

$^1$H NMR (Acetone-D6, 500 MHz) δ: 8.63 (s, 1H), 7.35-7.55 (m, 2H), 7.31-7.34 (m, 7H), 7.19 (d, J=1.5 Hz, 1H), 7.14 (d, J=16.5 Hz, 1H), 7.09 (d, J=16.5 Hz, 1H), 7.03 (dd, J=8.0, 1.5 Hz, 1H), 6.84 (d, J=8.0 Hz, 1H), 6.02 (s, 2H), 4.45 (s, 2H). $^{13}$C NMR (Acetone-D6, 125 MHz) δ: 149.3, 148.3, 138.6, 134.4, 133.1, 131.9, 130.7, 129.3, 129.2, 128.5, 128.1, 127.1, 122.4, 120.6, 120.5, 109.2, 106.1, 102.2, 57.9.

Example 26: Preparation of E-4-(N,N-dimethyl-amino-sulfonamino)-3',4'-methylenedioxy-stilbene (LSS-17)

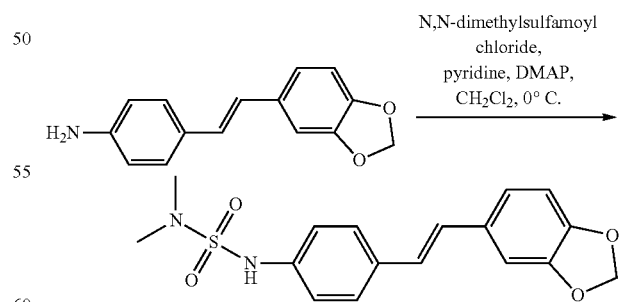

The compound WS-4 (0.83 mmol, 0.20 g) and DMAP (0.083 mmol, 0.01 g) are added to a 100 mL round-bottom flask and dissolved with anhydrous dichloromethane (20 mL); pyridine (2.49 mmol, 0.2 mL) and dimethylsulfamoyl chloride (2.49 mmol, 0.27 mL) are added drop by drop at room temperature to react at room temperature for 6 days. At the end of the reaction, the dichloromethane is evaporated off and then a saturated NaHCO$_3$ solution (25 mL) is added and stirred for 0.5 h. Additional 30 mL of dichloromethane is added for extraction, and the organic layer at the bottom is washed with water (20 mL), and then washed with saturated brine (25 mL), concentrated by rotary evaporation, and dried to obtain a solid substance. The solid substance is subjected to column chromatography (200-300-mesh silica gel, mobile phase being subject to V (dichloromethane): V (methanol)=10:0.1) to obtain a faint yellow powdered solid compound LSS-17 (0.020 g, yield 6.93%).

$^1$H NMR (Acetone-D6, 500 MHz) δ: 8.77 (s, 1H), 7.51-7.54 (m, 2H), 7.33-7.35 (m, 2H), 7.18 (d, J=1.5 Hz, 1H), 7.11 (d, J=16.5 Hz, 1H), 7.06 (d, J=16.5 Hz, 1H), 7.01 (dd, J=8.0, 2.0 Hz, 1H), 6.84 (d, J=8.0 Hz, 1H), 6.01 (s, 2H), 2.79 (s, 6H). $^{13}$C NMR (Acetone-D6, 125 MHz) δ: 149.2, 148.2, 138.9, 134.2, 133.1, 128.3, 127.9, 127.1, 122.3, 120.9, 109.1, 106.1, 102.1, 38.4.

Example 27: Preparation of E-4-((4-N, N-dimethylamino)-benzoylamino)-3',4'-methylenedioxy-stilbene

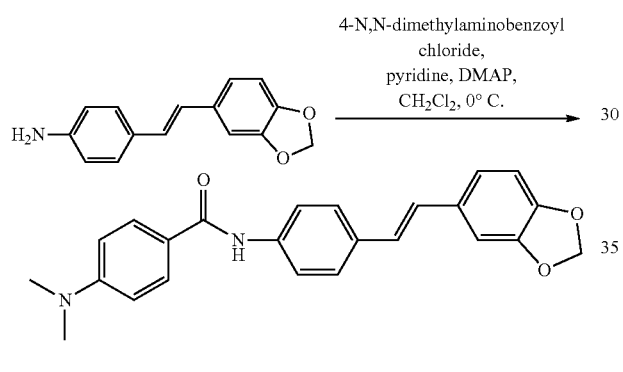

Using the method of Example 6, WS-4 reacts with 4-N, N-dimethylaminobenzoyl chloride to obtain the above target compound.

Example 28: Preparation of E-4-(1-cyanocyclopropylformamino)-3',4'-methylenedioxy-stilbene

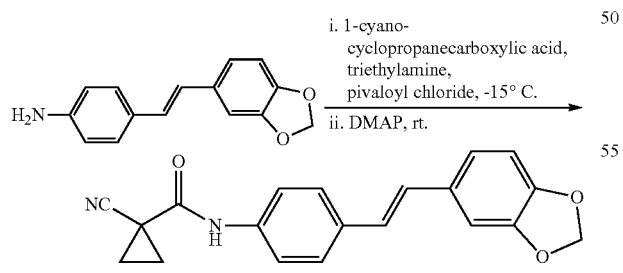

Using the method of Example 10, WS-4 reacts with 1-cyano-cyclopropanecarboxylic acid to obtain the above target compound.

$^{13}$C NMR (DMSO-D6, 125 MHz) δ: 163.7, 147.9, 146.9, 137.3, 133.3, 131.7, 127.4, 126.4, 126.1, 121.4, 121.1, 120.0, 108.3, 105.2, 101.0, 17.0, 14.8.

Example 29: Preparation of E-4-(6-methoxy-2-naphthoylamino)-3',4'-methylenedioxy-stilbene

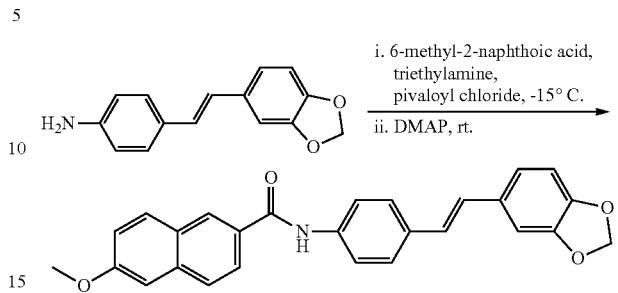

Using the method of Example 10, WS-4 reacts with 6-methoxy-2-naphthoic acid to obtain the above target compound.

Example 30: Preparation of E-4-(5-methyl-2-thiophenecarboxamino)-3',4'-methylenedioxy-stilbene

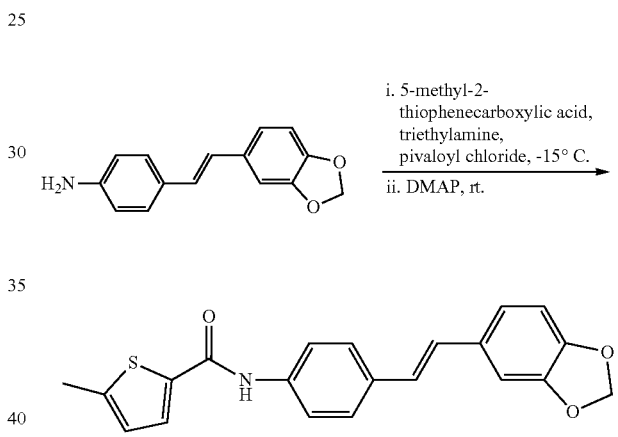

Using the method of Example 10, WS-4 reacts with 5-methyl-2-thiophenecarboxylic acid to obtain the above target compound.

Example 31: Preparation of E-4-(6-fluoropyridine-2-carboxamino)-3',4'-methylenedioxy-stilbene

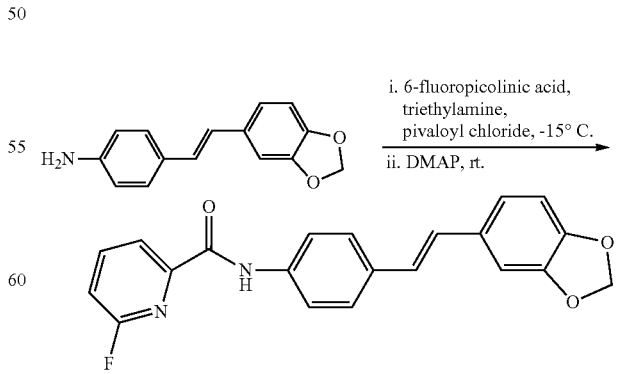

Using the method of Example 10, WS-4 reacts with 6-fluoropicolinic acid to obtain the above target compound.

Example 32: Preparation of E-4-(2-methylquinolin-6-carboxamino)-3',4'-methylenedioxy-stilbene

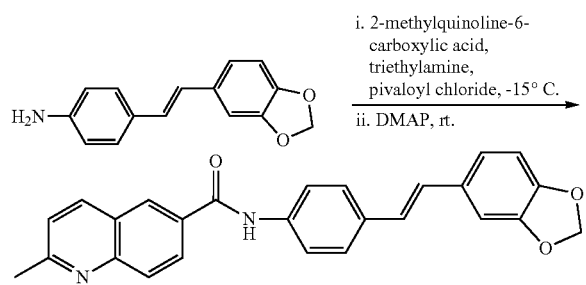

Using the method of Example 10, WS-4 reacts with 2-methylquinoline-6-carboxylic acid to obtain the above target compound.

Embodiment 33: Example 22: Preparation of E-4-(2-tetrahydrofurancarboxamino)-3',4'-methylenedioxy-stilbene

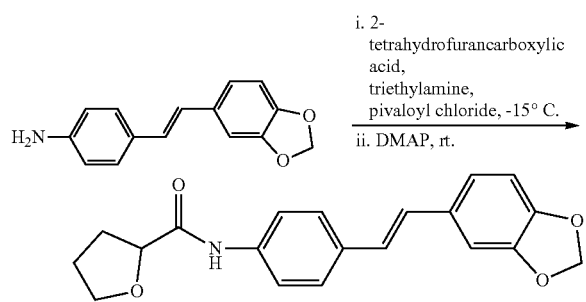

Using the method of Example 10, WS-4 reacts with 2-tetrahydrofurancarboxylic acid to obtain the above target compound.

Example 34: Preparation of E-4-(N-methylpiperidine-4-carboxamino)-3',4'-methylenedioxy-stilbene Hydrochloride

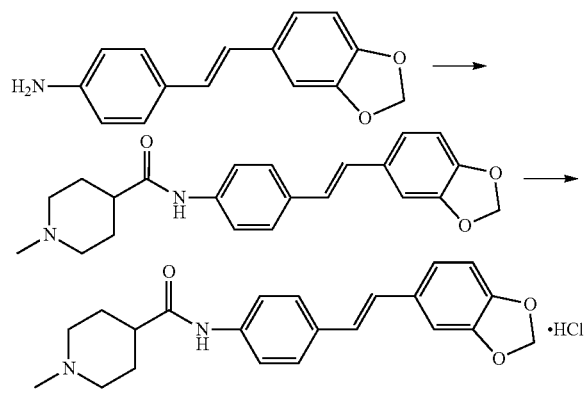

Using the method of Example 10, WS-4 reacts with 1-methylpiperidine-4-carboxylic acid to obtain a compound E-4-(N-methylpiperidine-4-carboxamino)-3',4'-methylenedioxy-stilbene. The compound is dissolved in chloroform, a methanol solution of HCl is added dropwise, and the solution is filtered and precipitated to obtain the above target compound.

Example 35: In Vitro Cytotoxicity Experiment the Experimental Cell Line is HEK293

Experimental Method:

Cells are cultured in a 96-well plate at a cell concentration of 5000/well. After 24 hours of cell culture, the drug treatment is performed and the experiment is carried out on two groups: the control group is added with DMSO with the same concentration as that for the experimental group; in the experimental group, each compound is tested at three doses of low, medium and high doses (100 µM; 500 µM; 1000 µM), and five parallels are tested at each dose; in the blank group, a complete medium is added with a compound to be tested with the same concentration as that for the experimental group. Constant temperature incubation is carried out for 24 h in a $CO_2$ incubator, MTT with a final concentration of 0.5 mg/mL is then added; 4 hours later, 200 µL of DMSO solution is added, and the absorbance is measured at 490 nm. The cell survival is calculated according to the absorbance; Survival %=(Average concentration−Blank concentration)/(Average control concentration−Blank concentration)* 100%.

Figure 3:
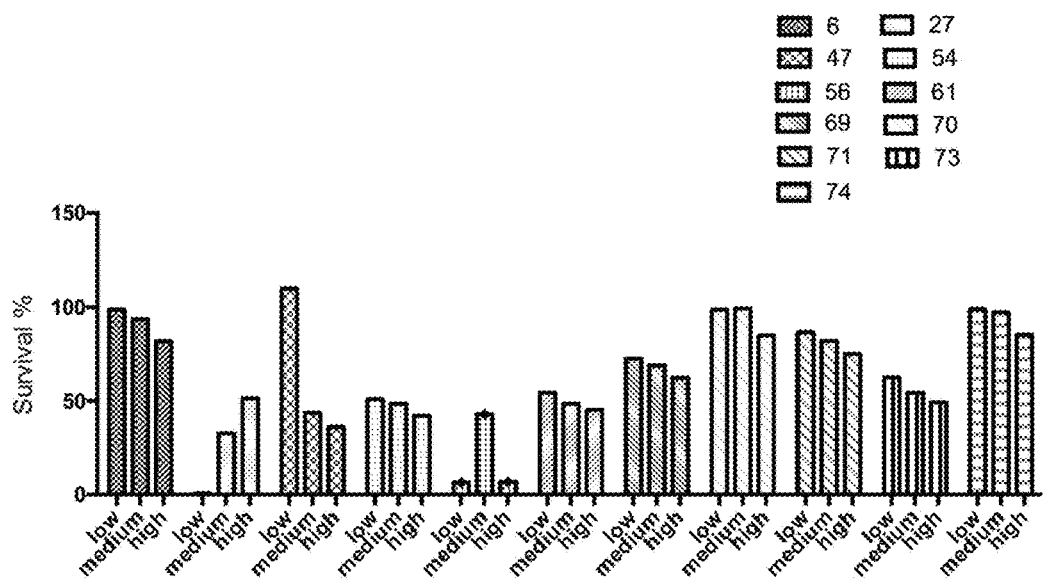
FIG. 3 is an in vitro cytotoxicity test chart of a novel stilbene derivative according to an example of embodiments of the present invention.

Reference is made to FIG. 3 which illustrates an in vitro cytotoxicity test chart of a novel stilbene derivative according to an example of embodiments of the present invention. FIG. 3 shows the effects of different compounds on cell survival. Compounds WS-27, i.e., pterostilbene (E-4-hydroxy-3',5'-dimethoxy-stilbene) and WS-56 (E-Conversion of 4-acetoxy-3',5'-dimethoxy-stilbene) are converted to acylaminos to obtain WS-61 (E-4-acetylamino-3',5'-dimethoxy-stilbene), which can reduce neurotoxicity, while the compounds of the general formula I and the general formula II, such as WS-6 (E-4-acetylamino-3',4'-methylenedioxy-stilbene) is further reduced in neurotoxicity as compared with WS-61. Other compounds of the general formulas I and II, such as WS-54 (E-4-isobutyrylamino-3',4'-methylenedioxy-stilbene), WS-69 (E-4-methylsulfonamino-3',4'-methylenedioxy-stilbene), WS-70 (E-4-benzoylamino-3',4'-methylenedioxy-stilbene), WS-71 (E-3,4-methylenedioxy-3'-fluoro-4'-acetylamino-stilbene), WS-73 (E-4-(2-thienyl)formamino-3',4'-methylenedioxy-stilbene), WS-74 (E-4-cyclopropylcarboxamino-3',4'-methylenedioxy-diphenyl Ethylene), generally have low neurotoxicity.

Example 36: Detection of Neurogenesis in Rat Hippocampus by BrdU (5-Bromo-2-deoxy Uridine, 5-bromodeoxyuridine) Labeling Experimental animals: 10-week-old SD male rats having a body weight of about 300 g are purchased. The rats are used in experiments one week after being adapted to the environment in an animal room. Experimental groups: control group, drug group. 2-3 rats per group. Experimental reagent: injection oil is used to dissolve a compound to be tested. Rates in the control group are injected with the same dose of dissolving oil.

Test method: intraperitoneal injection is carried out 28 days at the injection dose of 0.5 ml-1 ml each time. Dose: 4 mg/Kg.

Experimental Steps:

1) marker injection: BrdU (dissolved in sterile saline solution at a concentration of 10 mg/mL) solution is injected intraperitoneally into rats. (For rats with different body weights, the injection dose of BrdU is 50 mg·Kg$^{-1}$, injection is carried out twice every 2 hour; the intraperitoneal injection 24 hours before anesthesia ends.

2) Anesthesia: Anesthesia is performed by intraperitoneal injection of sodium pentobarbital solution into rats. (For rats with different body weights, the injection dose of sodium pentobarbital is usually 70 mg·Kg$^{-1}$.)

3) Cardiac perfusion: cardiac perfusion with normal saline is performed according to a general method.

4) Taking of brain tissues: The heads of the rats are separated from the bodies with surgical forceps and scissors, and then the muscles and membrane tissues at the top of the skulls are removed and brains are then gently peeled from the skulls. The separated brains are soaked in 4% paraformaldehyde for 24-48 hours.

5) Dehydration of brain tissues: the fixed tissues are soaked with a 20% sucrose PBS solution for more than 72 hours, and then the brain tissues are soaked with a 30% sucrose PBS solution for more than 72 hours.

6) Frozen section: the brain tissues are cut into 30 nm thick sections by a general coronal section procedure.

7) DAB immunohistochemistry step: DNA denaturation is carried out and the sections are transferred to a 24-well plate (pH 7.4) perfused with 0.1 M PBS. The brain sections are incubated with 1% $H_2O_2$ for 30 minutes to remove horseradish peroxidase; the sections are then treated with a 2M HCl solution for 30 minutes at room temperature to denature them. After completion of the denaturation, the brain sections are immersed in a 0.1 M sodium borate (pH 8.5) solution for 5 minutes and rinsed twice; the brain sections are incubated in 0.5% PBST for 1 hour at room temperature, and then are blocked for 1 hour with a serum blocking solution on a shaker at room temperature, and the serum blocking solution is from the same source as a secondary antibody; the samples are treated on the shaker with a BrdU primary antibody overnight at 4° C., and the BrdU primary antibody is diluted with the blocking solution; the samples are incubated with the biotinylated secondary antibody IgG for 2 hours at room temperature; a C (ABC kit) solution is incubated at room temperature for 2 hours; finally, after 3 to 5 minutes of color development by the DAB kit, the samples are mounted by using a PVP mounting medium and then dried, and finally the experimental results are detected under a microscope.

Figure 4:
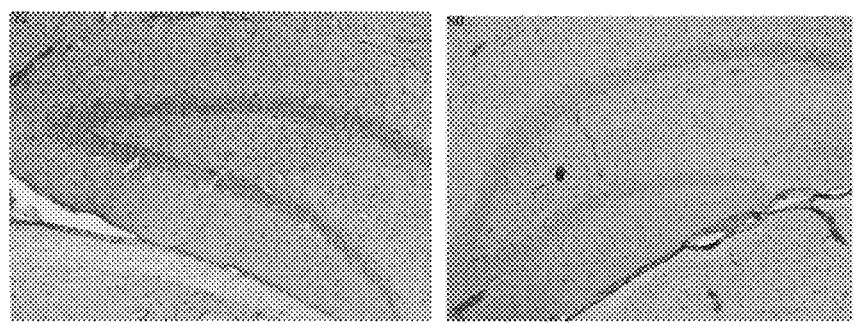
FIGS. 4(a)-(b) are DAB immunohistochemistry microscope views of a novel stilbene derivative according to an example of embodiments of the present invention.
Figure 5:
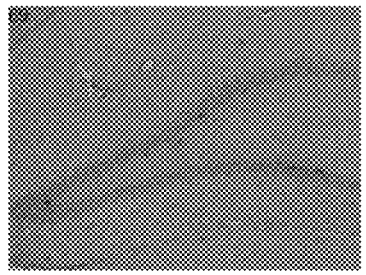
FIGS. 5(a)-(c) are DAB immunohistochemistry microscope views of a novel stilbene derivative according to an example of embodiments of the present invention.
Figure 5:
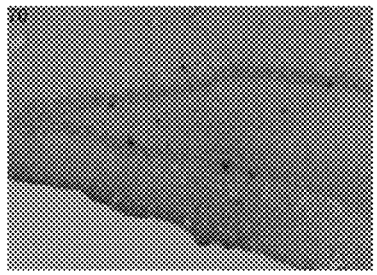
Figure 5:
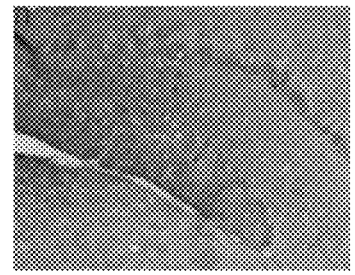
Figure 6:
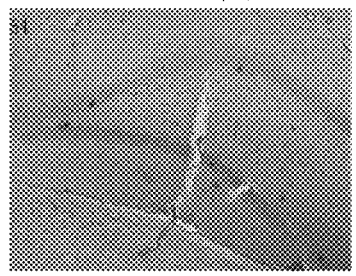
FIGS. 6(a)-(c) are DAB immunohistochemistry microscope views of a novel stilbene derivative according to an example of embodiments of the present invention.
Figure 6:
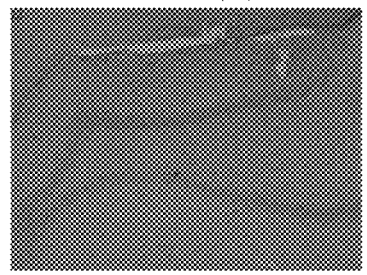
Figure 6:

Reference is made to FIGS. 4-6 which illustrate microscope views of a novel stilbene derivative of one example of the embodiments of the present invention.

FIG. 4 shows microscope views of the BrdU labeling of proliferating neurons that are promoted by compounds in the rat hippocampus, the compounds are similar to the structure of the embodiment of the present invention, where FIG. 4(a) is a BrdU labeling diagram of a control compound WS-77, and FIG. 4(b) is a BrdU labeling diagram of a reference compound WS-80.

Compared with the control group, the BrdU labeling results of the compounds are as follows:

The BrdU labeling result of WS-77 is positive, indicating that the diphenylacetylene analogue of WS-6 still maintains neurogenesis activity to some degree, while the BrdU labeling result of WS-80 is negative, indicating that the unsubstituted hydrogen atoms on the amides of general formulae I and II are important for neurogenesis activity.

FIG. 5 shows microscope views of the BrdU labeling of novel stilbene derivatives according to an example of the embodiments of the present invention for promoting neurogenesis in the rat hippocampus, where FIG. 5(a) is a BrdU labeling diagram of WS-69, FIG. 5(b) is a BrdU labeling diagram of WS-70, and FIG. 5(c) is a BrdU labeling diagram of WS-71.

The BrdU labeling results of the compounds WS-69, WS-70, WS-71 are positive.

FIG. 6 shows microscope views of the BrdU labeling of novel stilbene derivatives according to an example of the embodiments of the present invention for promoting neurogenesis in the rat hippocampus, where FIG. 6(a) is a BrdU labeling diagram of WS-54, FIG. 65(b) is a BrdU labeling diagram of WS-73, and FIG. 7(c) is a BrdU labeling diagram of WS-74.

BrdU labeling results of compounds WS-54, WS-73, WS-74 are positive.

Figure 7:
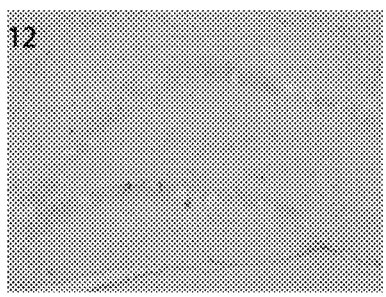
FIGS. 7(a)-(c) are DAB immunohistochemistry microscope views of a novel stilbene derivative according to an example of embodiments of the present invention.
Figure 7:
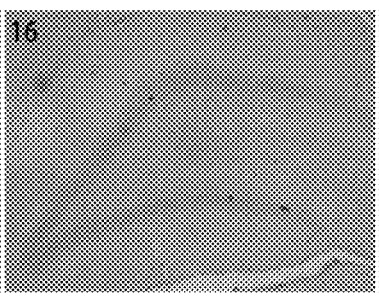
Figure 7:
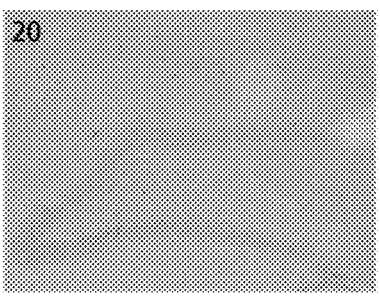

FIG. 7 shows microscopic views of the BrdU labeling of novel stilbene derivatives according to an example of the embodiments of the present invention for promoting neurogenesis in the rat hippocampus, where FIG. 7(a) is a BrdU labeling diagram of LSS-12, FIG. 5(b) is a BrdU labeling diagram of LSS-16, and FIG. 5(c) is a BrdU labeling diagram of LSS-20.

The BrdU labeling results of the compounds LSS-12, LSS-16 and LSS-20 are positive.

Figure 8:
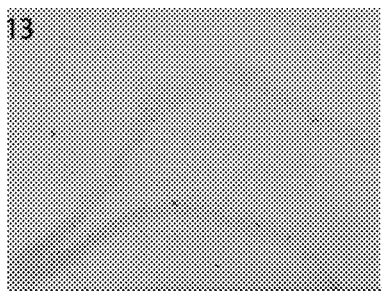
FIGS. 8(a)-(c) are DAB immunohistochemistry microscope views of a novel stilbene derivative according to an example of embodiments of the present invention.
Figure 8:
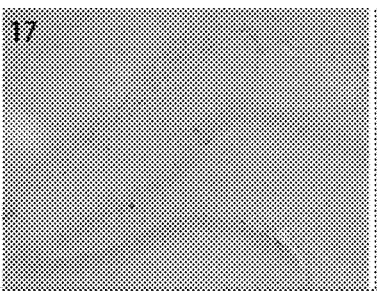
Figure 8:
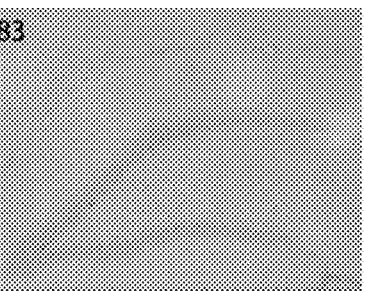

FIG. 7 shows microscopic views of the BrdU labeling of novel stilbene derivatives according to an example of the embodiments of the present invention for promoting neurogenesis in the rat hippocampus, where FIG. 8(a) is a BrdU labeling diagram of LSS-13, FIG. 8(b) is a BrdU labeling diagram of LSS-17, and FIG. 8(c) is a BrdU labeling diagram of WS-83.

The BrdU labeling results of the compounds LSS-13, LSS-17 and WS-83 are positive.

Example 37: Experimental Procedure of BrdU and NeuN Fluorescence Double Staining The samples are obtained in the same manner as an Example 34. First, the DNA denaturation is performed, and the sections are transferred to a HCl solution perfused with 2 N, and treated at 37° C. for 60 minutes to be denatured. After completion of the denaturation, the brain sections are immersed in a 0.1 M sodium borate (pH 8.5) solution for 5 minutes and rinsed twice; the brain sections are then blocked for 1 hour with a serum blocking solution on a shaker at room temperature, and the serum blocking solution is from the same source as a secondary antibody; the samples are treated on the shaker with BrdU (1:500, Millipore) and NeuN (1:500, Abcam) primary antibodies overnight at 4° C., and the primary antibodies are diluted with the blocking solution; the samples are incubated with fluorescent secondary antibodies goat anti-mouse and goat anti-rabbits at room temperature (1:50, Zhongshanjinqiao) for 2 hours at room temperature in a dark place; the samples are mounted by using a fluorescent anti-quenching PVP mounting medium and then dried, and finally the experimental results are detected under a microscope. Control group and drug group (low dose L, 2 mg/Kg; medium dose M, 4 mg/Kg).

Figure 9:
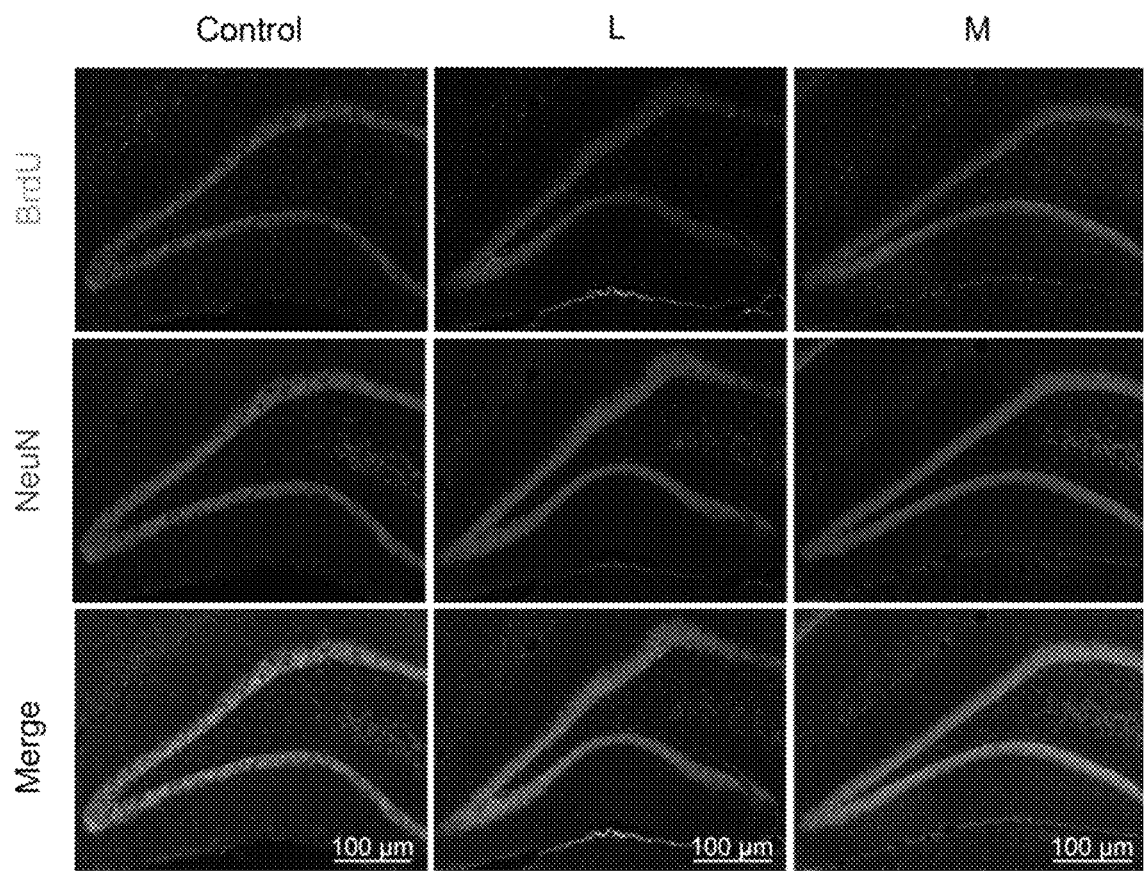
FIG. 9 is a graph showing a BrdU and NeuN fluorescence double staining experiment test of a novel stilbene derivative according to an example of embodiments of the present invention.

FIG. 9 is a graph showing a BrdU and NeuN fluorescence double staining experiment test of a novel stilbene derivative WS-6 (E-4-acetylamino-3',4'-methylenedioxy-stilbene) according to an example of embodiments of the present invention. From FIG. 7, cells (BrdU positive) promoted to proliferate by the compound WS-6 are neural cells (NeuN positive), that is to say, WS-6 can promote neurogenesis; and there is a dose-structure-activity relationship in WS-6, NeuN+BrdU+ spots at a low dose (2 mg/Kg) are more than NeuN$^+$BrdU$^+$ spots at a high dose (4 mg/Kg), indicating that WS-6 can further enhance neurogenesis at the dose of 4 mg/Kg over the dose of 2 mg/Kg.

Example 38

The dose-effect relationships of different compounds is further tested according to the method of Example 36, and the compounds include WS-54 (E-4-isobutyrylamino-3',4'-methylenedioxy-stilbene), WS-69 (E-4-Methylsulfonamino-3',4'-methylenedioxy-stilbene), WS-70 (E-4-Benzamino-3',4'-methylenedioxy-stilbene), and WS-74 (E-4-Cyclopropylformamino-3',4'-methylenedioxy-stilbene).

Figure 10:
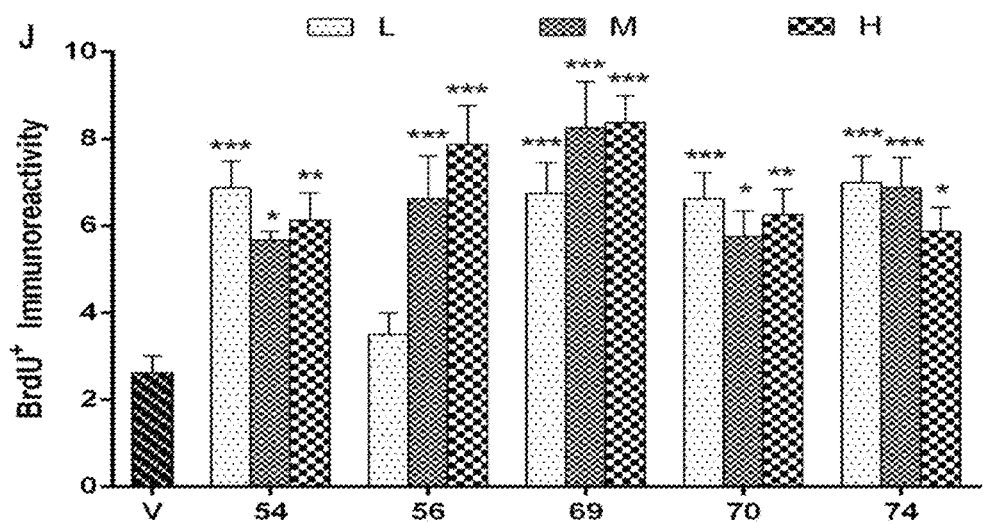
FIG. 10 is a graph showing a dose-effect relationship test of a novel stilbene derivative according to an example of embodiments of the present invention.

FIG. 10 is a graph showing a dose-effect relationship test of a novel stilbene derivative according to an example of embodiments of the present invention. Referring to FIG. 10, compared with WS-56 (E-4-acetoxy-3',5'-dimethoxy-stilbene) which is an acetylated derivative of pterostilbene, the compounds claimed by the present patent, such as WS54. WS-69, WS-70 and WS-74, still have significant activities of proliferation promotion (BrdU positive) at a low dose (0.5 mg/Kg), whereas WS-56 has no significant activity as compared with a blank sample (V). This shows the importance of the substituents (i.e., amides and methylene dioxygens) of the compounds of the general formulae I and II for the activity of the stilbene compounds. (V: blank sample; L: low dose 0.5 mg/Kg; M: Medium dose 1.0 mg/Kg; H: high dose 4.0 mg/Kg; *P<0.05; P<0.01; *P<0.001)

Example 39: Preparation of E-4-(1-pyrrolidinyl) formamino-3',4'-methylenedioxy-stilbene

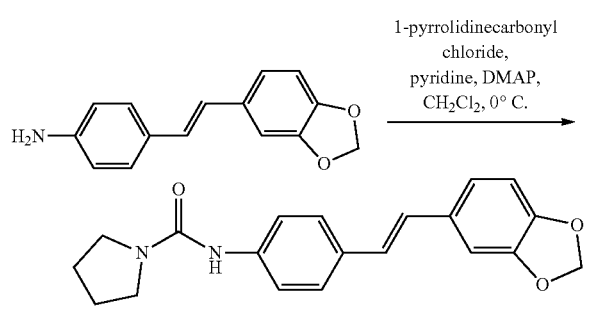

Using the method of Example 6, WS-4 reacts with 1-pyrrolidinecarbonyl chloride to obtain the above target compound.

For the method embodiments, for simplicity of description, they are all expressed as a series of operation combinations, but those skilled in the art should understand that the present invention is not limited by the described operation sequence because some steps can be carried out in other orders or at the same time according to the present invention. Second, those skilled in the art should also understand that the embodiments described in the specifications are all preferred embodiments, and the involved operating and experimental conditions are not necessarily required by the present invention.

A novel stilbene derivative and a preparation method of the novel stilbene derivative provided by the present invention have been described above in details. Specific examples are used herein to describe the principle and implementations of the present application. The above description of the embodiments is only used to help understand the method of the present application and its core concept. Moreover, for those skilled in the art, based on the concept of the present application, there will be changes in the specific embodiments and application scope. In summary, the contents of the present specification should not be understood as intending to limit the present application

What is claimed is:

1. A stilbene derivative, wherein the stilbene derivative is a compound of the following formula I or formula II, or an acceptable salt formed by the compound of the formula I or the formula II and an inorganic or organic acid;

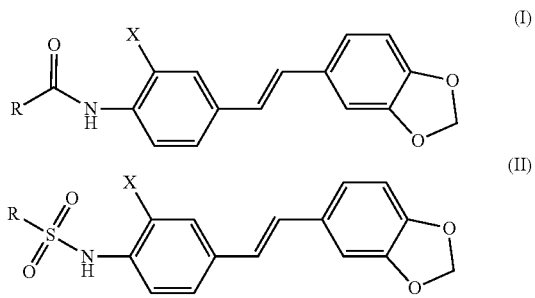

wherein, in the formula I or the formula II, wherein X is a hydrogen atom or a halogen atom;
R is C1-C6 alkyl, 1-6-membered heteroalkyl, C2-C4 alkenyl, C2-C4 alkynyl, C3-C6 cycloalkyl, substituted C3-C6 cycloalkyl, 3-6-membered heterocycloalkyl, substituted 3-6-membered heterocycloalkyl, 5-18-membered aryl, substituted 5-18-membered aryl, 5-18-membered heteroaryl, or substituted 5-18-membered heteroaryl;
wherein in the substituted C3-C6 cycloalkyl, the substituted 3-6-membered heterocycloalkyl, the substituted 5-18-membered aryl, and the substituted 5-18-membered heteroaryl, the substitution refers to the C3-C6 cycloalkyl, the 3-6-membered heterocycloalkyl, the 5-18-membered aryl, and the 5-18-membered heteroaryl are substituted with at least one of the following substituents: aryl, heteroaryl, C3-C6 cycloalkyl, 3-6-membered heterocycloalkyl, C1-C6 alkyl, C2-C4 alkenyl, C2-C4 alkynyl, 1-6-membered heteroalkyl, nitro, cyano, hydroxy, halogen, amino.

2. The stilbene derivative according to claim 1, wherein X is a hydrogen atom or a fluorine atom;
the R is C1-C4 alkyl, 3-5-membered heteroalkyl, C3-C6 cycloalkyl, substituted C3-C6 cycloalkyl, 3-6-membered heterocycloalkyl, and substituted 3-6-membered heterocycloalkyl, 6-10-membered aryl, substituted 6-10-membered aryl, 5-10-membered heteroaryl, or substituted 5-10-membered heteroaryl;
wherein in the substituted C3-C6 cycloalkyl, the substituted 3-6-membered heterocycloalkyl, the substituted 6-10-membered aryl, and the substituted 5-10-membered heteroaryl, the substitution refers to the C3-C6 cycloalkyl, the 3-6-membered heterocycloalkyl, the 6-10-membered aryl, and the 5-10-membered heteroaryl are substituted with at least one of the following substituents: aryl, heteroaryl, C3-C6 cycloalkyl, 3-6-membered heterocycloalkyl, C1-C6 alkyl, C2-C4 alkenyl, C2-C4 alkynyl, 1-6-membered heteroalkyl, nitro, cyano, hydroxy, halogen, amino.

3. The stilbene derivative according to claim 2, wherein
the C1-C4 alkyl is methyl, ethyl, n-propyl, isopropyl or tert-butyl;
the 3-5-membered heteroalkyl is N,N-dimethylamino, N-methyl-N-ethylamino, N,N-dimethylaminomethyl, N,N-diethylamino, methoxy, ethoxy, isopropoxy or tert-butoxy;
the C3-C6 cycloalkyl is cyclopropyl, cyclobutyl, cyclopentyl or cyclohexyl;
the substituted C3-C6 cycloalkyl is methylcyclopropyl, fluorocyclopropyl, cyanocyclopropyl, cyclopropylmethyl or (cyclohexyl)ethyl;
the 3-6-membered heterocycloalkyl is tetrahydrofuranyl, pyrrolidinyl, morpholinyl, piperidinyl, or piperazinyl;
the substituted 3-6-membered heterocycloalkyl is N-methylpiperidinyl, N-ethylpiperidinyl, N-acetylpiperidinyl, or (N-methylpiperidinyl) piperidinyl;
the 6-10 membered aryl is phenyl or naphthyl;
the substituted 6-10-membered aryl is substituted phenyl or substituted naphthyl;
the 5-10-membered heteroaryl is furyl, pyrrolyl, thienyl, pyridyl, quinolinyl or isoquinolinyl;
the substituted 5-10-membered heteroaryl is substituted furyl, substituted pyrrolyl, substituted thienyl, substituted pyridyl, substituted quinolinyl, or substituted isoquinolinyl;
the substituted phenyl is methylphenyl, dimethylphenyl, fluorophenyl, chlorophenyl, bromophenyl, isopropylphenyl, tertiary aminophenyl, methoxyphenyl, dimethoxyphenyl, acetylphenyl, cyanophenyl, (R)-1-phenyl-1-1-methoxymethyl, (S)-1-phenyl-1-methoxymethyl, benzyl, methoxybenzyl, methylbenzyl, tertiary aminobenzyl, fluorobenzyl, chlorobenzyl, or cyanobenzyl;
the substituted naphthyl is methoxynaphthyl, methylnaphthyl, tertiary aminonaphthyl, fluoronaphthyl, chloronaphthyl, or cyanonaphthyl;
the substituted furyl is methoxyfuryl, methylfuryl, fluorofuryl, chlorofuryl or cyanofuryl;
the substituted thienyl is methoxythienyl, methylthienyl, fluorothienyl, chlorothienyl or cyanothienyl;
the substituted pyridyl is methylpyridyl, methoxypyridyl, fluoropyridyl, chloropyridyl, cyanopyridyl, pyridylmethyl, (pyridyl)ethyl or (pyridylsulfydryl)methyl;
the substituted quinolinyl is methoxyquinolinyl, methylquinolinyl, fluoroquinolinyl, chloroquinolinyl, or cyanoquinolinyl;
the substituted isoquinolinyl is methoxyisoquinolinyl, methylisoquinolinyl, fluoroisoquinolinyl, chloroisoquinolinyl or cyanoisoquinolinyl.

4. The stilbene derivative according to claim 2, wherein
the substituted C3-C6 cycloalkyl is a substituted C3 cycloalkyl;
the 3-6-membered heterocycloalkyl is 5-6-membered heterocycloalkyl;
the 6-10 membered aryl is 6-membered aryl;
the substituted 6-10-membered aryl is substituted 6-membered aryl;
the 5-10-membered heteroaryl is a 5-6-membered heteroaryl;
the substituted 5-10-membered heteroaryl is substituted 6-membered heteroaryl;
wherein in the substituted C3-C6 cycloalkyl, the substituted 6-10-membered aryl, and the substituted 5-10-membered heteroaryl, the substitution refers to the C3-C6 cycloalkyl, the 6-10-membered aryl, and the 5-10-membered heteroaryl are substituted with at least one of the following substituents: aryl, heteroaryl, C3-C6 cycloalkyl, 3-6-membered heterocycloalkyl, C1-C6 alkyl, C2-C4 alkenyl, C2-C4 alkynyl, 1-6-membered heteroalkyl, nitro, cyano, hydroxy, halogen, amino.

5. The stilbene derivative according to claim 4, wherein
the C1-C4 alkyl is methyl, ethyl, n-propyl or isopropyl;
the 3-5-membered heteroalkyl is N,N-dimethylamino;
the C3-C6 cycloalkyl is cyclopropyl or cyclobutyl;
the 6-membered aryl is phenyl.

6. The stilbene derivative according to claim 4, wherein
the C1-C4 alkyl is tert-butyl;
the C3-C6 cycloalkyl is cyclopentyl or cyclohexyl;
the substituted C3 cycloalkyl is cyanocyclopropyl;
the 5-6-membered heterocycloalkyl is pyrrolidinyl;
the 3-5 membered heteroalkyl is N-methyl-N-ethylamino, N,N-dimethylaminomethyl, N,N-diethylamino, methoxy, ethoxy, isopropoxy or tert-butoxy;
the 5-6-membered heteroaryl is thienyl or pyridyl;
the substituted 6-membered aryl is benzyl, methylphenyl, fluorophenyl, chlorophenyl, or cyanophenyl;
the substituted 6-membered heteroaryl is pyridinylmethyl;
the C2-C4 alkenyl is vinyl or propenyl;
the C2-C4 alkynyl is ethynyl or propynyl.

7. The stilbene derivative according to claim 2, wherein
the substituted C3-C6 cycloalkyl is methylcyclopropyl, fluorocyclopropyl, cyclopropylmethyl or (cyclohexyl)ethyl;
the 3-6-membered heterocycloalkyl is tetrahydrofuranyl, pyrrolidinyl, morpholinyl, piperidinyl, or piperazinyl;
the substituted 3-6-membered heterocycloalkyl is N-methylpiperidinyl, N-ethylpiperidinyl, N-acetylpiperidinyl, or (N-methylpiperidinyl) piperidinyl;
the 6-10-membered aryl is naphthyl;
the substituted 6-10-membered aryl is substituted phenyl or substituted naphthyl;
the 5-10-membered heteroaryl is furyl, pyrrolyl, quinolinyl or isoquinolinyl;
the substituted 5-10-membered heteroaryl is substituted furyl, substituted pyrrolyl, substituted thienyl, substituted pyridyl, substituted quinolinyl, or substituted isoquinolinyl;
the substituted phenyl is dimethylphenyl, bromophenyl, isopropylphenyl, tertiary aminophenyl, methoxyphenyl, dimethoxyphenyl, acetylphenyl, (R)- 1-phenyl-1-methoxymethyl, (S)-1-phenyl-1-methoxymethyl, benzyl, methoxybenzyl, methylbenzyl, tertiary aminobenzyl, fluorobenzyl, chlorobenzyl, or cyanobenzyl;
the substituted naphthyl is methoxynaphthyl, methylnaphthyl, tertiary aminonaphthyl, fluoronaphthyl, chloronaphthyl, or cyanonaphthyl;
the substituted furyl is methoxyfuryl, methylfuryl, fluorofuryl, chlorofuryl or cyanofuryl;
the substituted thienyl is methoxythienyl, methylthienyl, fluorothienyl, chlorothienyl or cyanothienyl;
the substituted pyridyl is methylpyridyl, methoxypyridyl, fluoropyridyl, chloropyridyl, cyanopyridyl, (pyridyl)ethyl or (pyridylsulfydryl)methyl;
the substituted quinolinyl is methoxyquinolinyl, methylquinolinyl, fluoroquinolinyl, chloroquinolinyl, or cyanoquinolinyl;

the substituted isoquinolinyl is methoxyisoquinolinyl, methylisoquinolinyl, fluoroisoquinolinyl, chloroisoquinolinyl or cyanoisoquinolinyl.

8. A stilbene derivative, wherein the stilbene derivative is a compound of the following formula I or formula II or an acceptable salt formed by the compound of the formula I or the formula II and an inorganic or organic acid;

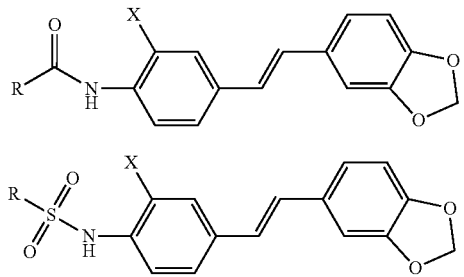

wherein, in the formula I or the formula II, X is a hydrogen atom or a halogen atom;
R is a substituted C2-C4 alkenyl;
Wherein in the substituted C2-C4 alkenyl, the substitution refers to the C2-C4 alkenyl is substituted with at least one of the following substituents: aryl, heteroaryl, C3-C6 cycloalkyl, 3-6-membered heterocycloalkyl, C1-C6 alkyl, C2-C4 alkenyl, C2-C4 alkynyl, 1-6-membered heteroalkyl, nitro, cyano, hydroxy, halogen, amino.

9. The stilbene derivative according to claim 8, wherein the substituted C2-C4 alkenyl is 2,2-dialkylvinyl, 6-membered arylvinyl, substituted 6-membered arylvinyl, or 5-6-membered heteroarylvinyl.

10. The stilbene derivative according to claim 9, wherein the 2,2-dialkylvinyl is 2,2-dimethylvinyl;
the 6-membered aryl is phenylvinyl;
the substituted 6-membered arylvinyl is p-tolylvinyl, p-fluorophenylvinyl, p-cyanophenylvinyl or p-chlorophenylvinyl;
the 5-6-membered heteroaryl is pyridylvinyl.

11. The stilbene derivative according to claim 1, wherein the compound of the formula I or the formula II is prepared by acylating E-4'-amino-3,4-methylenedioxy-stilbene or E-3,4-methylenedioxy-3'-fluoro-4'-amino-stilbene with an acylating agent;
the acylating agent is a carboxylic acid, an anhydride or an acyl chloride;
the carboxylic acid is 2-furancarboxylic acid, 2-thiophenecarboxylic acid, 2-picolinic acid, 2-tetrahydrofurancarboxylic acid, (R)-2-tetrahydrofurancarboxylic acid, (S)-2-tetrahydrofuran Formic acid, 1-methylpiperidine-4-carboxylic acid, cyclopropylacetic acid, 1-methylcyclopropanecarboxylic acid, 2-methylcyclopropanecarboxylic acid, 1-cyanocyclopropanecarboxylic acid, cyclopropylacetic acid, or cyclobutyric acid;
the anhydride is benzoic anhydride, acetic anhydride, propionic anhydride, n-butyric anhydride, isobutyric anhydride, benzoic anhydride or di-tert-butyl dicarbonate;
the acyl chloride is pivaloyl chloride, N,N-dimethylcarbamoyl chloride, benzenesulfonyl chloride, cyclopropylsulfonyl chloride, isopropylsulfonyl chloride, 4-methoxybenzoyl chloride, 4-cyanobenzoyl chloride, 4-chlorobenzenesulfonyl chloride, phenylacetyl chloride, benzylsulfonyl chloride, p-toluenesulfonyl chloride, 1-pyrrolidinecarbonyl chloride, N-acetylpiperidin-4-chloride, isopropyl chloroformate, dimethylamino sulfonyl chloride, or 4-dimethylaminobenzoyl chloride.

12. The stilbene derivative according to claim 11, wherein the compound of the formula I or the formula II is prepared by acylating the E-4'-amino-3,4-methylenedioxy-stilbene with the acylating agent;
when the carboxylic acid is 2-thiophenecarboxylic acid, 2-picolinic acid, cyclopropylacetic acid, cyclobutyric acid, 2-tetrahydrofurancarboxylic acid, or 1-methylpiperidine-4-carboxylic acid, the structural formula of the compound is any of the following i-vi:

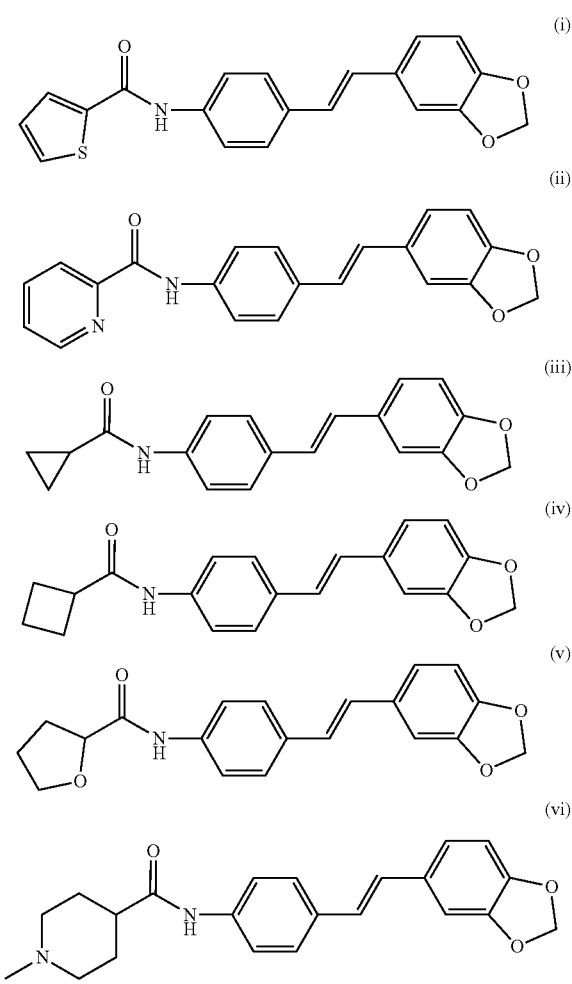

when the anhydride is acetic anhydride, propionic anhydride, n-butyric anhydride, isobutyric anhydride, benzoic anhydride, or di-tert-butyl dicarbonate, the structural formula of the compound is any of the following vii-xii:

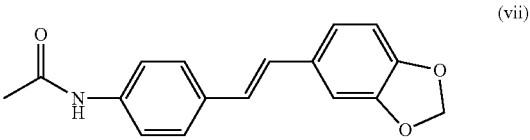

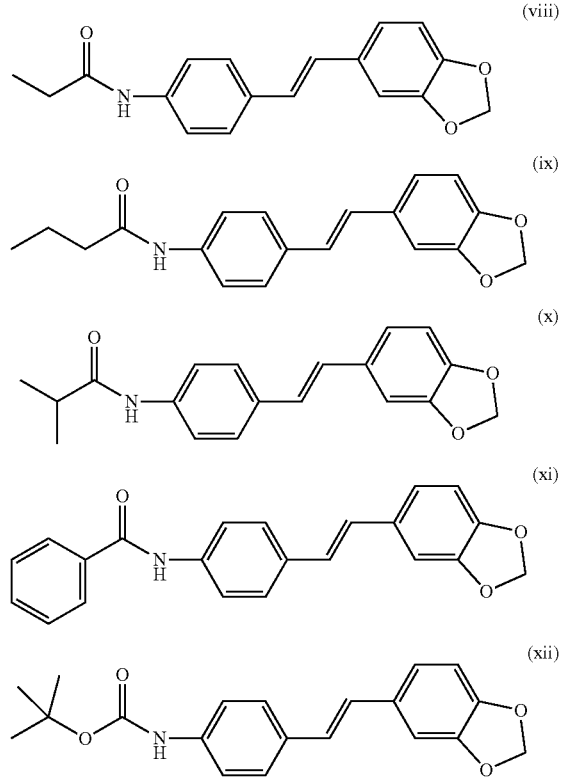

when the acyl chloride is p-toluenesulfonyl chloride, N,N-dimethylcarbamoyl chloride, benzenesulfonyl chloride, pivaloyl chloride, cyclopropylsulfonyl chloride, isopropylsulfonyl chloride, 4-methoxybenzoyl chloride, 4-cyanobenzoyl chloride, 4-chlorobenzenesulfonyl chloride, phenylacetyl chloride, benzylsulfonyl chloride, isopropyl chloroformate, dimethylaminosulfonyl chloride or 4-dimethylaminobenzoyl chloride, the structural formula of the compound is any of the following xiii-xxvi:

(xxvi)

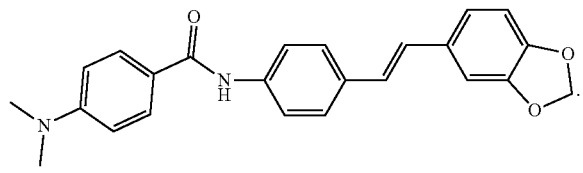

13. The stilbene derivative according to claim 11, wherein the compound of the formula I or the formula II is prepared by acylating E-3,4-methylenedioxy-3'-fluoro-4'-amino-stilbene with an acylating agent;

when the carboxylic acid is cyclopropylacetic acid, cyclobutyric acid or 2-picolinic acid, the structural formula of the compound is any of the following xxvii-xxix:

(xxvii)

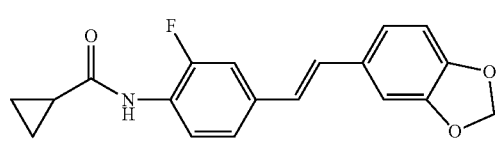

(xxviii)

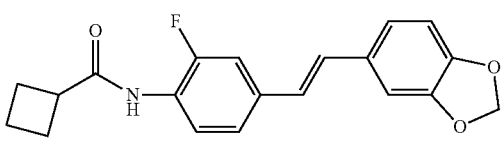

(xxix)

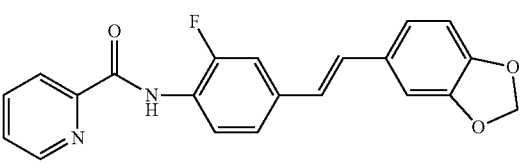

when the anhydride is acetic anhydride, isobutyric anhydride or benzoic anhydride, the structural formula of the compound is any of the following xxx-xxxii:

(xxx)

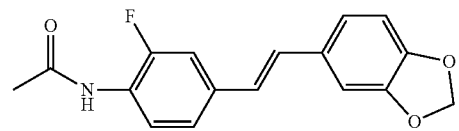

(xxxi)

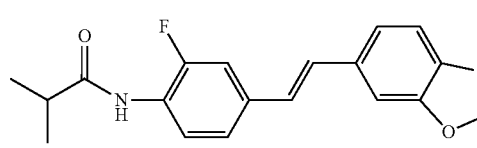

(xxxii)

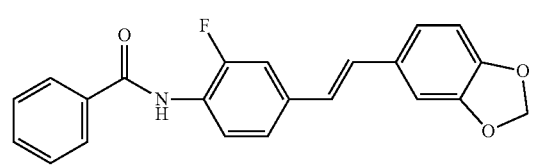

when the acyl chloride is N, N-dimethylcarbamoyl chloride, methylsulfonyl chloride, cyclopropylsulfonyl chloride, isopropylsulfonyl chloride, dimethylsulfamoyl chloride, or benzenesulfonyl chloride, the structural formula of the compound is any of the following xxxiii-xxxviii:

(xxxiii)

(xxxiv)

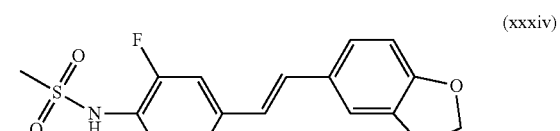

(xxxv)

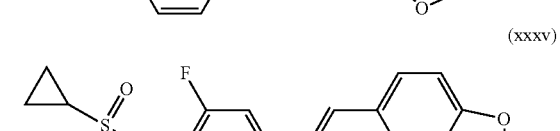

(xxxvi)

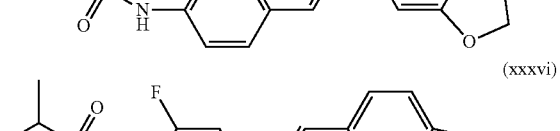

(xxxvii)

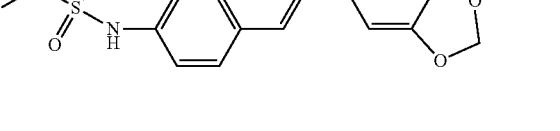

(xxxviii)

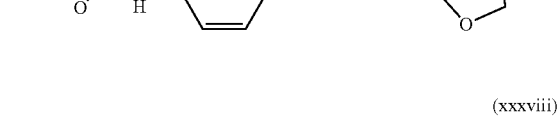

14. The stilbene derivative according to claim 1, wherein the compound of the formula I or the formula II is prepared by acylating E-4'-amino-3, 4-methylenedioxy-stilbene or E-3, 4-methylenedioxy-3'-fluoro-4'-amino-stilbene with an acylating agent;

the acylating agent is acryloyl chloride;

the acylating agent is cyclopentylcarboxylic acid.

15. The stilbene derivative according to claim 14, wherein the compound of the formula I or the formula II is prepared by acylating E-4'-amino-3,4-methylenedioxy-stilbene with an acylating agent;

when the acylating agent is acryloyl chloride, the structural formula of the compound is:

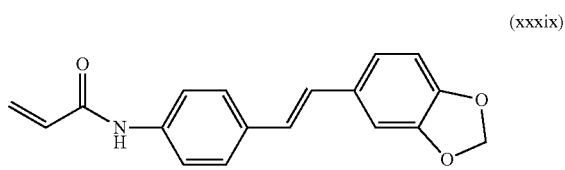 [SMILES: C=CC(=O)Nc1ccc(/C=C/c2ccc3c(c2)OCO3)cc1]
(xxxix)

when the acylating agent is cyclopentylcarboxylic acid, the structural formula of the compound is:

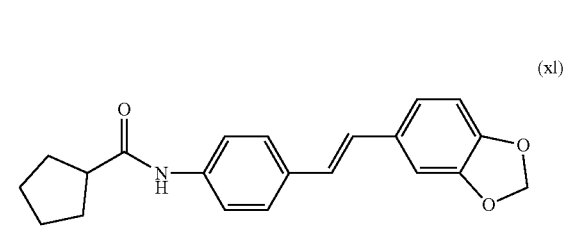 [SMILES: O=C(Nc1ccc(/C=C/c2ccc3c(c2)OCO3)cc1)C1CCCC1]
(xl)

the compound of the formula I or the formula II is prepared by acylating E-3,4-methylenedioxy-3'-fluoro-4'-amino-stilbene with an acylating agent;

when the acylating agent is acryloyl chloride, the structural formula of the compound is:

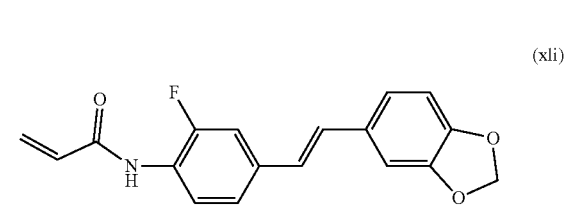 [SMILES: C=CC(=O)Nc1ccc(/C=C/c2ccc3c(c2)OCO3)cc1F]
(xli)

when the acylating agent is cyclopentylcarboxylic acid, the structural formula of the compound is:

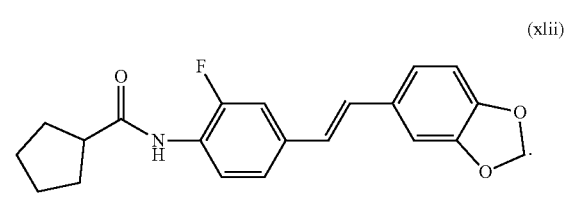 [SMILES: O=C(Nc1ccc(/C=C/c2ccc3c(c2)OCO3)cc1F)C1CCCC1]
(xlii)

16. The stilbene derivative according to claim 8, wherein the compound of the formula I or the formula II is prepared by Page 12 of 18 acylating E-4'-amino-3,4-methylenedioxy-stilbene or E-3,4-methylenedioxy-3'-fluoro-4'-amino-stilbene with an acylating agent;

the acylating agent is a carboxylic acid, an anhydride or an acyl chloride.

17. The stilbene derivative according to claim 16, wherein the compound of the formula I or the formula II is prepared by acylating the E-4'-amino-3,4-methylenedioxy-stilbene with the acylating agent;

when the carboxylic acid is p-fluorophenylacrylic acid, p-cyanophenylacrylic acid or pyridylacrylic acid, the structural formula of the compound is any of the following xliii-xlv:

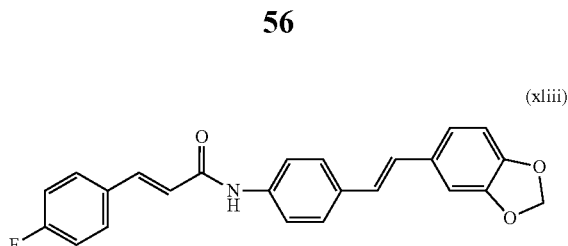
(xliii)

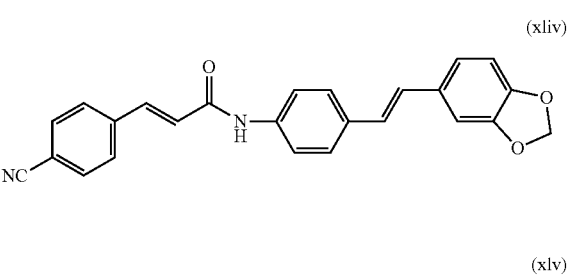
(xliv)

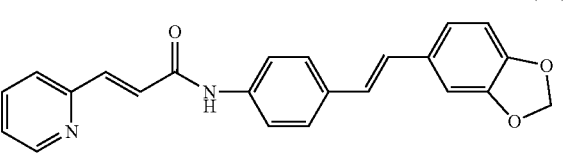
(xlv)

when the acyl chloride is 3,3-dimethylacryloyl chloride, cinnamoyl chloride, p-tolylacryloyl chloride or p-chlorophenylacryloyl chloride, the structural formula of the compound is any of the following xlvi-xlix:

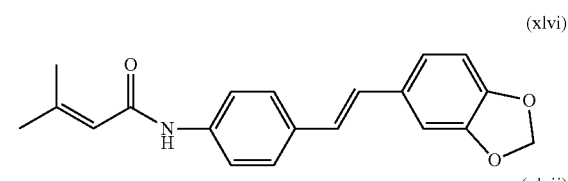
(xlvi)

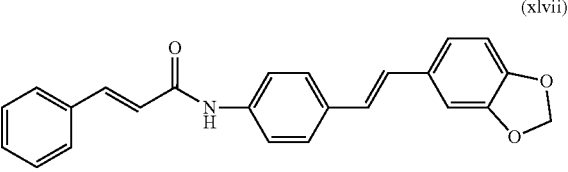
(xlvii)

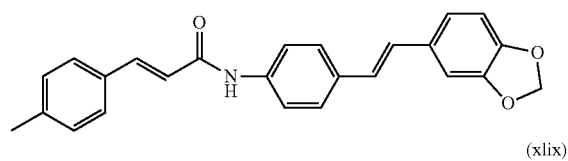
(xlviii)

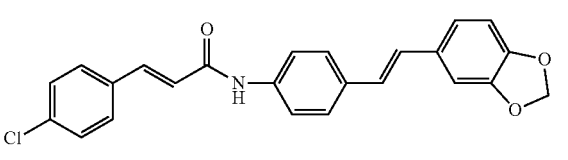
(xlix)

the compound of the formula I or the formula II is prepared by acylating E-3,4-methylenedioxy-3'-fluoro-4'-amino-stilbene with an acylating agent;

when the acyl chloride is cinnamoyl chloride, the structural formula of the compound is:

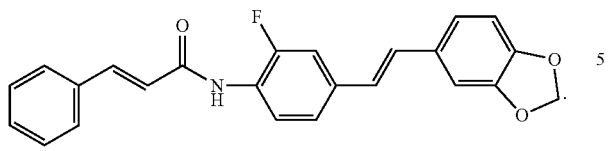

(I)

18. The stilbene derivative according to claim 1, wherein the inorganic acid is hydrochloric acid, sulfuric acid, hydrobromic acid, hydroiodic acid or phosphoric acid; the organic acid is acetic acid, malonic acid, methanesulfonic acid, succinic acid, p-toluenesulfonic acid, citric acid, maleic acid or tartaric acid.

19. The stilbene derivative according to claim 8, wherein the inorganic acid is hydrochloric acid, sulfuric acid, hydrobromic acid, hydroiodic acid or phosphoric acid; the organic acid is acetic acid, malonic acid, methanesulfonic acid, succinic acid, p-toluenesulfonic acid, citric acid, maleic acid or tartaric acid.

20. A method for treating Alzheimer's disease and treating neurodegenerative diseases, wherein the method comprises administering to a patient a therapeutically effective dose of the stilbene derivative according to claim 1 or a pharmaceutically acceptable salt thereof.

\* \* \* \* \*